(12) United States Patent
Chan et al.

(10) Patent No.: US 6,989,897 B2
(45) Date of Patent: Jan. 24, 2006

(54) METAL COATED NANOCRYSTALLINE SILICON AS AN ACTIVE SURFACE ENHANCED RAMAN SPECTROSCOPY (SERS) SUBSTRATE

(75) Inventors: Selena Chan, San Jose, CA (US); Andrew A. Berlin, San Jose, CA (US); Sunghoon Kwon, Santa Clara, CA (US); Narayanan Sundararajan, San Francisco, CA (US); Mineo Yamakawa, Campbell, CA (US)

(73) Assignee: Intel Corporation, Santa Clara, CA (US)

(*) Notice: Subject to any disclaimer, the term of this patent is extended or adjusted under 35 U.S.C. 154(b) by 0 days.

(21) Appl. No.: 10/680,583

(22) Filed: Oct. 7, 2003

(65) Prior Publication Data

US 2004/0135997 A1   Jul. 15, 2004

Related U.S. Application Data

(63) Continuation-in-part of application No. 10/171,357, filed on Jun. 12, 2002, and a continuation-in-part of application No. 10/368,976, filed on Feb. 18, 2003.

(51) Int. Cl.
    *G01J 3/44* (2006.01)
(52) U.S. Cl. .................................... 356/301; 356/244
(58) Field of Classification Search ................ 356/301, 356/244
    See application file for complete search history.

(56) References Cited

U.S. PATENT DOCUMENTS

| | | | |
|---|---|---|---|
| 5,255,067 A | 10/1993 | Carrabba et al. | |
| 5,306,403 A | 4/1994 | Vo-Dinh | |
| 5,561,304 A | * 10/1996 | Canham et al. | ............. 313/503 |
| 5,567,628 A | 10/1996 | Tarcha et al. | |
| 5,770,022 A | 6/1998 | Chang et al. | |
| 5,994,164 A | 11/1999 | Fonash et al. | |
| 6,002,471 A | 12/1999 | Quake | |

(Continued)

FOREIGN PATENT DOCUMENTS

EP   0984269 A1   3/2000

(Continued)

OTHER PUBLICATIONS

Schoenfeld, et al., "Formation of Si Quantum Dots in Nanocrystalline Silicon," Proc. 7th Int. Conf. On Modulated Semiconductor Structures, Madrid, pp. 605-608, 1995.

(Continued)

*Primary Examiner*—Gregory J. Toatley, Jr.
*Assistant Examiner*—Kara Geisel
(74) *Attorney, Agent, or Firm*—DLA Piper Rudnick Gray Cary US LLP

(57) ABSTRACT

The disclosed methods and apparatus concern Raman spectroscopy using metal coated nanocrystalline porous silicon substrates. Porous silicon substrates may be formed by anodic etching in dilute hydrofluoric acid. A thin coating of a Raman active metal, such as gold or silver, may be coated onto the porous silicon by cathodic electromigration or any known technique. In certain alternatives, the metal coated porous silicon substrate comprises a plasma-oxidized, dip and decomposed porous silicon substrate. The metal-coated substrate provides an extensive, metal rich environment for SERS, SERRS, hyper-Raman and/or CARS Raman spectroscopy. In certain alternatives, metal nanoparticles may be added to the metal-coated substrate to further enhance the Raman signals. Raman spectroscopy may be used to detect, identify and/or quantify a wide variety of analytes, using the disclosed methods and apparatus. In some disclosed methods, Raman spectroscopy may be used to detect nucleotides, purines or pyrimidines at the single molecule level.

29 Claims, 8 Drawing Sheets

U.S. PATENT DOCUMENTS

| | | |
|---|---|---|
| 6,017,773 A | 1/2000 | Fauchet et al. |
| 6,040,191 A | 3/2000 | Grow |
| 6,136,704 A | 10/2000 | Maya |
| 6,149,868 A | 11/2000 | Natan et al. |
| 6,153,489 A | 11/2000 | Park et al. |
| 6,171,945 B1 | 1/2001 | Mandal et al. |
| 6,174,677 B1 | 1/2001 | Vo-Dinh |
| 6,180,415 B1 | 1/2001 | Schultz et al. |
| 6,249,080 B1 | 6/2001 | Komoda et al. |
| 6,268,041 B1 | 7/2001 | Goldstein |
| 6,294,442 B1 | 9/2001 | Kamal |
| 6,300,193 B1 | 10/2001 | Forbes |
| 6,312,768 B1 | 11/2001 | Rode et al. |
| 6,313,914 B1 | 11/2001 | Roe |
| 6,322,895 B1 | 11/2001 | Canham |
| 6,344,272 B1 | 2/2002 | Oldenburg et al. |
| 6,358,613 B1 | 3/2002 | Buriak |
| 6,358,815 B2 | 3/2002 | Maeda |
| 6,359,276 B1 | 3/2002 | Tu |
| 6,376,177 B1 | 4/2002 | Poponin |
| 6,399,177 B1 | 6/2002 | Fonash et al. |
| 6,478,974 B1 | 11/2002 | Lebouitz et al. |
| 6,504,292 B1 * | 1/2003 | Choi et al. .................. 313/310 |
| 6,623,977 B1 * | 9/2003 | Farquharson et al. ....... 356/301 |
| 2002/0020053 A1 | 2/2002 | Fonash et al. |
| 2002/0142480 A1 * | 10/2002 | Natan ......................... 356/301 |

FOREIGN PATENT DOCUMENTS

| | | | |
|---|---|---|---|
| GB | 590479 | | 7/1947 |
| GB | 2 373 367 A | | 9/2002 |
| WO | WO 00/08445 | * | 2/2000 |
| WO | 03/106943 A1 | | 12/2003 |

OTHER PUBLICATIONS

Unal, et al. "Photovoltaic Properties of a Novel Stain Etched Porous Silicon and its Application in Photosensitive Devices," *Optical Materials*, 17 (2001) 79-82.

Vo-Dinh, "Surface-Enhanced Raman Spectroscopy Using Metallic Nanostructures," *Trends in Analytical Chemistry*, vol. 17, Nos. 8-9, 1998.

Cai, et al., "Optical Properties of Ag and Au Nanoparticles Dispersed within the Pores of Monolithic Mesoporous Silica," *J. Nanoparticle Res.* 3:443-453, 2001.

Cai, et al., "Direct Formation of Self-Assembled Nanoporous Aluminium Oxide in $SiO_2$ and Si Substrates," *Nanotechnology* 13:627, 2002.

Chan, et al., "Tunable, Narrow and Directional Luminescence From Porous Silicon Light Emitting Devices," *Applied Physics Lett*. 75:274-276, 1999.

Duffy, et al., "Rapid Prototyping of Microfluidic Systems in Poly(dimethylsiloxane)," *Anal. Chem*. 70:49747-84, 1998.

Varghese, et al., "Highly Ordered Nanoporous Alumina Films: Effect of Pore Size and Uniformity on Sensing Performance," *J. Mater. Res*. 17:1162-1171, 2002

Weiping, et al. "Synthesis and Structural and Optical Properties of Mesoporous Silica Containing Silver Nanoparticles," *J. Phys. Condens, Matter* 9: 7257-7267, 1997.

Parbukov et al., "The production of a novel stain-etched porous silicon, metallization of the porous surface and application in hydrocarbon sensors", *Materials Science and Engineering*, C15(1-2):121-123 (2001).

Canham, "Silicon quantum wire array fabrication by electrochemical and chemical dissolution of wafers," Appl. Phys. Lett. 57:1046, 1990.

Collins et al., Physics Today 50:24-31, 1997.

Cullis et al. J. Appl. Phys. 82:909-965, 1997.

Edelberg, et al., "Visible luminescence from nanocrystalline silicon films produced by plasma enhanced chemical vapor deposition," Appl. Phys. Lett., 68:1415-1417, 1996.

Feldheim , "Assembly of metal nanoparticles arrays using moleuclar bridges," The Electrochemical Society Interface, Fall, 2001, pp. 22-25.

Gole et al., "Patterned metallization of porous silicon from electroless solution for direct electrical contact," J. Electrochem. Soc. 147:3785, 2000.

Henneke, "Porous Silicon: theories behind light emission," 1996, 1-4. Retrieved from the Internet URL: <http://neon.utexas.edu/academic/course/Fall 1997/CH380L/student.papers/dh.html>.

Jin et al., "Photoinduced conversion of silver nanspheres to nanoprisms," Science 294:1901, 2001.

Lopez and Fauchet, "Erbium emission form porous silicon one-dimensional photonic band gap structures," Appl. Phys. Lett. 77:3704-6, 2000.

Lutzen et al., Structural characteristics of ultrathin nanocrystalline silicon films formed by annealing amorphous silicon, J. Vac. Sci Technology B 16:2802-05, 1998.

Petrova-Koch et al., "Rapid-thermal-oxidized porous silicon—the superior photoluminescent Si," Appl. Phys. Lett. 61:943, 1992.

* cited by examiner

US 6,989,897 B2

METAL COATED NANOCRYSTALLINE SILICON AS AN ACTIVE SURFACE ENHANCED RAMAN SPECTROSCOPY (SERS) SUBSTRATE

RELATED APPLICATIONS

The present application is a continuation-in-part of pending U.S. patent application Ser. No. 10/171,357, filed Jun. 12, 2002, and a continuation-in-part of pending U.S. patent application Ser. No. 10/368,976, filed Feb. 18, 2003.

FIELD

The present methods and apparatus relate to the fields of molecular detection and/or characterization by Raman spectroscopy. More particularly, the methods and apparatus concern metal-coated porous substrates for surface enhanced Raman spectroscopy (SERS), surface enhanced resonance Raman spectroscopy (SERRS), hyper-Raman and/or coherent anti-Stokes Raman spectroscopy (CARS).

BACKGROUND

The sensitive and accurate detection and/or identification of single molecules from biological and other samples has proven to be an elusive goal, with widespread potential uses in medical diagnostics, pathology, toxicology, environmental sampling, chemical analysis, forensics and numerous other fields. Attempts have been made to use Raman spectroscopy and/or surface plasmon resonance to achieve this goal. When light passes through a tangible medium, a certain amount becomes diverted from its original direction, a phenomenon known as Raman scattering. Some of the scattered light also differs in frequency from the original excitatory light, due to the absorption of light and excitation of electrons to a higher energy state, followed by light emission at a different wavelength. The wavelengths of the Raman emission spectrum are characteristic of the chemical composition and structure of the light absorbing molecules in a sample, while the intensity of light scattering is dependent on the concentration of molecules in the sample.

The probability of Raman interaction occurring between an excitatory light beam and an individual molecule in a sample is very low, resulting in a low sensitivity and limited applicability of Raman analysis. It has been observed that molecules near roughened silver surfaces show enhanced Raman scattering of as much as six to seven orders of magnitude. This surface enhanced Raman spectroscopy (SERS) effect is related to the phenomenon of plasmon resonance, wherein metal nanoparticles exhibit a pronounced optical resonance in response to incident electromagnetic radiation, due to the collective coupling of conduction electrons in the metal. In essence, nanoparticles of gold, silver, copper and certain other metals can function as miniature "antenna" to enhance the localized effects of electromagnetic radiation. Molecules located in the vicinity of such particles exhibit a much greater sensitivity for Raman spectroscopic analysis.

Attempts have been made to exploit SERS for molecular detection and analysis, typically by coating metal nanoparticles or fabricating rough metal films on the surface of a substrate and then applying a sample to the metal-coated surface. However, the number of metal particles that can be deposited on a planar surface is limited, producing a relatively low enhancement factor for SERS and related Raman techniques utilizing such surfaces. A need exists for methods of producing SERS-active substrates with higher densities of metal particles and apparatus comprising such substrates.

BRIEF DESCRIPTION OF THE DRAWINGS

The following drawings form part of the present specification and are included to further demonstrate certain aspects of the claimed methods and apparatus. The methods and apparatus may be better understood by reference to one or more of these drawings in combination with the detailed description presented herein.

FIG. 4A shows a porous silicon substrate.

FIG. 4B illustrates silicon oxidation, for example by plasma oxidation, to form a layer of silicon dioxide.

FIG. 4C shows immersion of the oxidized porous silicon in a metal salt solution, such as a silver nitrate solution.

FIG. 4D illustrates removal of excess metal salt solution.

FIG. 4E shows drying of the solution to form a thin layer of dry metal salt on the porous silicon substrate.

FIG. 4F illustrates thermal decomposition of the dry metal salt to form a uniform layer of metal coating the porous silicon substrate.

FIG. 6 shows the SERS emission spectra obtained with PODD silver-coated substrates of different porosities. The various spectra were obtained at average porosities, in order from the lowest trace to the highest trace, of 52%, 55%, 65%, 70% and 77%.

DESCRIPTION OF ILLUSTRATIVE EMBODIMENTS

Figure 1:
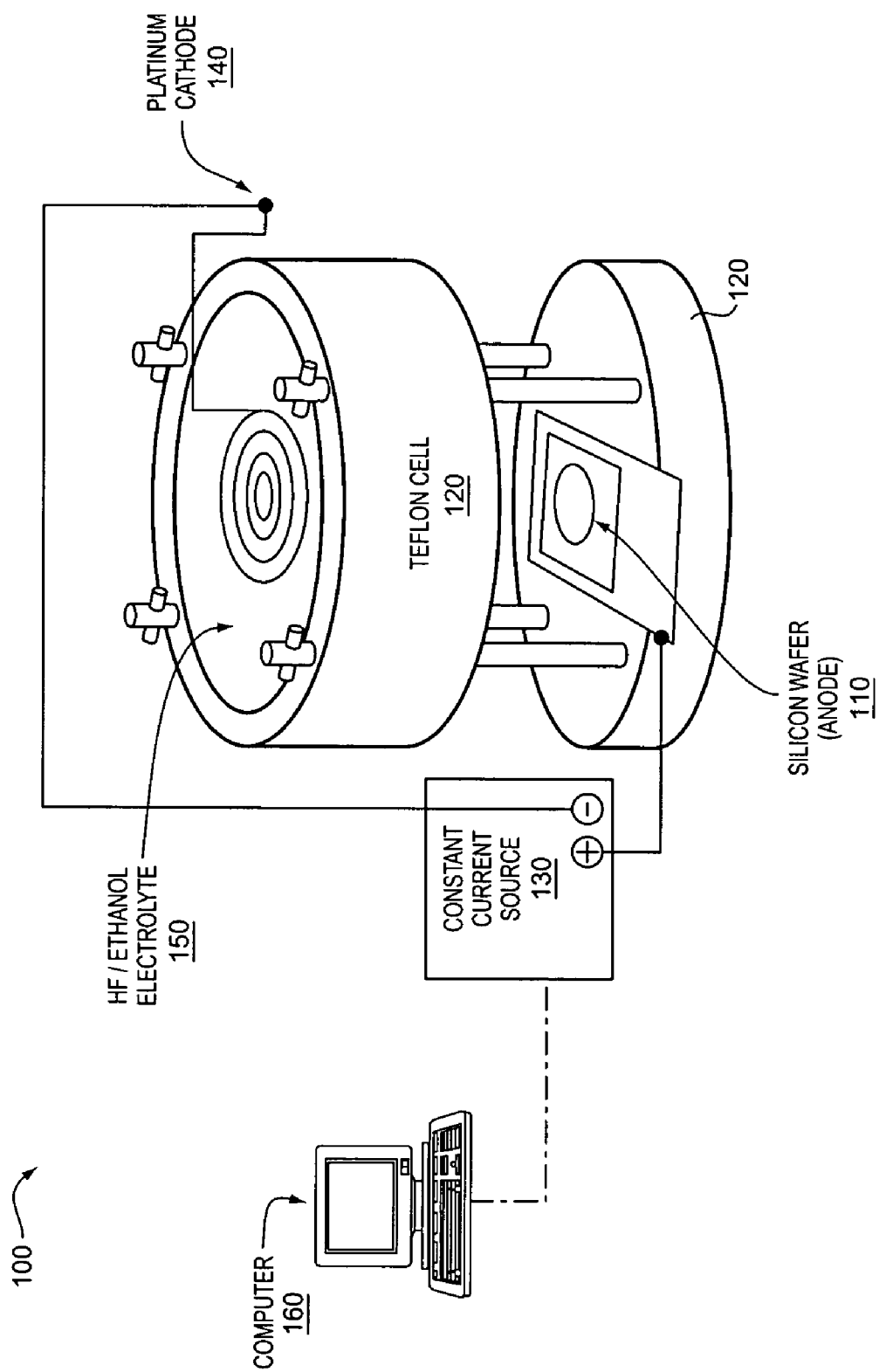
FIG. 1 illustrates an exemplary apparatus 100 (not to scale) and method for producing a porous silicon substrate 110.

The disclosed methods and apparatus are of use for the detection and/or identification of analytes by surface enhanced Raman spectroscopy (SERS), surface enhanced resonance Raman spectroscopy (SERRS) and/or coherent anti-Stokes Raman spectroscopy (CARS) detection. Compared to existing techniques, the disclosed methods and apparatus provide SERS active substrates with increased metal particle density, greater uniformity of metal deposition and greater depth of field of SERS enhancement, allowing more efficient Raman detection and/or identification of analytes.

Previous methods for SERS detection of various analytes have used colloidal metal particles, such as aggregated silver nanoparticles, that were typically coated onto a substrate and/or support (e.g., U.S. Pat. Nos. 5,306,403; 6,149,868; 6,174,677; 6,376,177). While such arrangements occasionally allow SERS detection with as much as $10^6$ to $10^8$ increased sensitivity, they are not capable of single molecule detection of small analytes such as nucleotides, as disclosed herein. Enhanced sensitivity of Raman detection is not uniform within a colloidal particle aggregate, but rather depends on the presence of "hot spots." The physical structure of such hot spots, the range of distances from the nanoparticles at which enhanced sensitivity occurs, and the spatial relationships between aggregate nanoparticles and analytes that allow enhanced sensitivity have not been characterized. Further, aggregated nanoparticles may be unstable in solution, with adverse effects on the reproducibility of single molecule analyte detection. The present methods and apparatus provide a stable microenvironment for SERS detection in which the physical conformation and density of the Raman-active metal substrate may be precisely controlled, allowing reproducible, sensitive and accurate detection of analytes in solution.

The following detailed description contains numerous specific details in order to provide a more thorough understanding of the claimed methods and apparatus. However, it will be apparent to those skilled in the art that the methods and/or apparatus may be practiced without these specific details. In other instances, devices, methods, procedures, and individual components that are well known in the art have not been described in detail herein.

Definitions

As used herein, "a" or "an" may mean one or more than one of an item.

As used herein, the term "analyte" means any atom, chemical, molecule, compound, composition or aggregate of interest for detection and/or identification. Non-limiting examples of analytes include an amino acid, peptide, polypeptide, protein, glycoprotein, lipoprotein, nucleoside, nucleotide, oligonucleotide, nucleic acid, sugar, carbohydrate, oligosaccharide, polysaccharide, fatty acid, lipid, hormone, metabolite, cytokine, chemokine, receptor, neurotransmitter, antigen, allergen, antibody, substrate, metabolite, cofactor, inhibitor, drug, pharmaceutical, nutrient, prion, toxin, poison, explosive, pesticide, chemical warfare agent, biohazardous agent, radioisotope, vitamin, heterocyclic aromatic compound, carcinogen, mutagen, narcotic, amphetamine, barbiturate, hallucinogen, waste product and/or contaminant. Analytes may be unlabeled or may be labeled with one or more Raman tags, as disclosed below.

A "capture" molecule is used herein to mean any molecule that may bind to one or more target analytes. Non-limiting examples of "capture" molecules include antibodies, antibody fragments, genetically engineered antibodies, single chain antibodies, receptor proteins, binding proteins, enzymes, inhibitor proteins, lectins, cell adhesion proteins, oligonucleotides, polynucleotides, nucleic acids and aptamers.

As used herein, the term "nanocrystalline silicon" refers to silicon that comprises nanometer-scale silicon crystals, typically in the size range from 1 to 100 nanometers (nm). "Porous silicon" refers to silicon that has been etched or otherwise treated to form a porous structure.

As used herein, "operably coupled" means that there is a functional interaction between two or more units of an apparatus and/or system. For example, a Raman detector may be "operably coupled" to a computer if the computer can obtain, process, store and/or transmit data on Raman signals detected by the detector.

Porous Substrates

Certain methods disclosed herein concern coating porous substrates with a uniform layer of one or more metals, such as Raman active metals. Although the porous substrates disclosed herein are porous silicon substrates, the claimed subject matter is not limited to those examples. Any porous substrate that is resistant to the application of heat may be used in the disclosed methods, systems and/or apparatus. Application of heat to about 300° C., 400° C., 500° C., 600° C., 700° C., 800° C., 900° C. or 1,000° C. is contemplated. The porous substrate may be rigid or flexible. A variety of porous substrates of potential use are known, including but not limited to porous silicon, porous polysilicon, porous metal grids and porous aluminum. Exemplary methods of making porous substrates are disclosed in further detail below.

Porous polysilicon substrates may be made by known techniques (e.g., U.S. Pat. Nos. 6,249,080 and 6,478,974). For example, a layer of porous polysilicon, may be formed on top of a semiconductor substrate by the use of low pressure chemical vapor deposition (LPCVD). The LPCVD conditions may include, for example, a pressure of about 20 pascal, a temperature of about 640° C. and a silane gas flow of about 600 sccm (standard cubic centimeters) (U.S. Pat. No. 6,249,080). A polysilicon layer may be etched, for example using electrochemical anodization with HF (hydrofluoric acid) or chemical etching with nitric acid and hydrofluoric acid, to make it porous (U.S. Pat. No. 6,478,974). Typically, porous polysilicon layers formed by such techniques are limited in thickness to about 1 μm (micrometer) or less. In contrast, porous silicon may be etched throughout the thickness of the bulk silicon wafer, which has a typical thickness of about 500 μm.

Porous aluminum substrates may also be made by known techniques (e.g., Cai et al., *Nanotechnology* 13:627, 2002; Varghese et al., *J. Mater. Res.* 17:1162–1171, 2002). For example, nanoporous aluminum oxide thin films may be fabricated on silicon or silicon dioxide using an electrochemical-assisted self-assembly process (Cai et al., 2002). The porous aluminum film may be thermally annealed to improve its uniformity (Cai et al., 2002). Alternatively, a thin layer of solid aluminum may be electrochemically anodized in dilute solutions of oxalic acid and/or sulfuric acid to create a nanoporous alumina film, (Varghese et al., 2002). The examples disclosed herein are not limiting and any known type of heat resistant porous substrate may be used. Such porous substrates may be uniformly impregnated with one or more metals, such as silver, using the methods disclosed herein.

Nanocrystalline Porous Silicon

Nanocrystalline Silicon

Certain exemplary apparatus disclosed herein may comprise one or more layers of nanocrystalline silicon. Various methods for producing nanocrystalline silicon are known in the art (e.g., Petrova-Koch et al., "Rapid-thermal-oxidized porous silicon—the superior photoluminescent Si," Appl. Phys. Lett. 61:943, 1992; Edelberg, et al., "Visible luminescence from nanocrystalline silicon films produced by plasma enhanced chemical vapor deposition," Appl. Phys. Lett., 68:1415–1417, 1996; Schoenfeld, et al., "Formation of Si quantum dots in nanocrystalline silicon," Proc. 7th Int. Conf. on Modulated Semiconductor Structures, Madrid, pp. 605–608, 1995; Zhao, et al., "Nanocrystalline Si: a material constructed by Si quantum dots," 1st Int. Conf. on Low Dimensional Structures and Devices, Singapore, pp. 467–471, 1995; Lutzen et al., Structural characteristics of ultrathin nanocrystalline silicon films formed by annealing amorphous silicon, J. Vac. Sci. Technology B 16:2802–05, 1998; U.S. Pat. Nos. 5,770,022; 5,994,164; 6,268,041; 6,294,442; 6,300,193). The methods and apparatus disclosed herein are not limited by the method of producing nanocrystalline silicon and it is contemplated that any known method may be used.

Non-limiting exemplary methods for producing nanocrystalline silicon include silicon (Si) implantation into a silicon rich oxide and annealing; solid phase crystallization with metal nucleation catalysts; chemical vapor deposition; PECVD (plasma enhanced chemical vapor deposition); gas evaporation; gas phase pyrolysis; gas phase photopyrolysis; electrochemical etching; plasma decomposition of silanes and polysilanes; high pressure liquid phase reduction-oxidation reactions; rapid annealing of amorphous silicon layers; depositing an amorphous silicon layer using LPCVD (low pressure chemical vapor deposition) followed by RTA (rapid thermal anneal) cycles; plasma electric arc deposition using a silicon anode and laser ablation of silicon (U.S. Pat. Nos. 5,770,022; 5,994,164; 6,268,041; 6,294,442; 6,300,193). Depending on the process, Si crystals of anywhere from 1 to 100 nm or more in size may be formed as a thin layer on a chip, a separate layer and/or as aggregated crystals. In certain methods and apparatus, a thin layer comprising nanocrystalline silicon attached to a substrate layer may be used.

In claimed methods and apparatus it is contemplated that nanocrystalline silicon may be used. However, the methods and apparatus are not limited as to the composition of the starting material, and in alternative methods and apparatus it is contemplated that other materials may be utilized, the only requirement being that the material must be capable of forming a porous substrate that can be coated with a Raman sensitive metal.

The size and/or shape of silicon crystals and/or pore size in porous silicon may be selected to be within predetermined limits, for example, in order to optimize the plasmon resonant frequency of metal-coated porous silicon (see, e.g., U.S. Pat. No. 6,344,272). The plasmon resonant frequency may also be adjusted by controlling the thickness of the metal layer coating the porous silicon (U.S. Pat. No. 6,344,272). Techniques for controlling the size of nano-scale silicon crystals are known (e.g., U.S. Pat. Nos. 5,994,164 and 6,294,442).

Porous Silicon

Certain claimed methods and apparatus concern use of a Raman active, metal-coated substrate. The substrate may comprise nanocrystalline porous silicon. As discussed above, the substrate is not limited to pure silicon, but may also comprise silicon nitride, germanium and/or other materials known for chip manufacture. Other minor amounts of material may also be present, such as metal nucleation catalysts and/or dopants. The only requirement is that the substrate material must be capable of forming a porous substrate that can be coated with a Raman sensitive metal. Porous silicon has a large surface area of up to 783 $m^2/cm^3$, providing a very large surface for surface enhanced Raman spectroscopy techniques.

Porous silicon was discovered in the late 1950's by electropolishing silicon in dilute hydrofluoric acid solutions. As is known in the art, porous silicon may be produced by etching of a silicon substrate with dilute hydrofluoric acid (HF) in an electrochemical cell. In certain cases, silicon may be initially etched in HF at low current densities. After the initial pores are formed, the silicon may be removed from the electrochemical cell and etched in very dilute HF to widen the pores formed in the electrochemical cell. The composition of the silicon substrate will also affect pore size, depending on whether or not the silicon is doped, the type of dopant and the degree of doping. The effect of doping on silicon pore size is known in the art. For detection and/or identification of large biomolecules, a pore size of about 2 nm to 100 or 200 nm may be selected. The orientation of pores in porous silicon may also be selected. For example, an etched 1,0,0 crystal structure will have pores oriented perpendicular to the crystals, while 1,1,1 or 1,1,0 crystal structures will have pores oriented diagonally along the crystal axis. The effect of crystal structure on pore orientation is known in the art. Crystal composition and porosity may also be regulated to change the optical properties of the porous silicon in order to enhance the Raman signals and decrease background noise. Optical properties of porous silicon are well known in the art (e.g., Cullis et al., J. Appl. Phys. 82:909–965, 1997; Collins et al., Physics Today 50:24–31, 1997).

FIG. 1 shows a non-limiting example of a method and apparatus 100 for producing a porous silicon substrate. A silicon wafer 110 is placed inside an electrochemical cell 120 comprising an inert material, such as Teflon®. The wafer 110 is connected to the positive pole of a constant current source 130, thus forming the anode 110 of the electrochemical cell 120. The negative pole of the constant current source 130 is connected to a cathode 140, such as a platinum cathode 140. The electrochemical cell 120 may be filled with a dilute electrolyte solution of HF 150 in ethanol. Alternatively, HF 150 may be dissolved in other alcohols and/or surfactants known in the art, such as pentane or hexane. A computer may be operably coupled to a constant current source 130 to regulate the current, voltage and/or time of electrochemical etching. The silicon wafer 110 exposed to HF electrolyte 150 in the electrochemical cell 120 becomes etched to form a porous silicon substrate 110. As is known in the art, the thickness of the porous silicon layer and the degree of porosity of the silicon may be controlled by regulating the time and/or current density of anodization and the concentration of HF 150 in the electrolyte solution (e.g., U.S. Pat. No. 6,358,815).

Portions of the silicon wafer 110 may be protected from HF 150 etching by coating with any known resist compound, such as polymethyl-methacrylate. Lithography methods, such as photolithography, of use for exposing selected portions of a silicon wafer 110 to HF 150 etching are well known in the art. Selective etching may be of use to control the size and shape of a porous Si chamber to be used for Raman spectroscopy. For some applications, a porous silicon chamber of about 1 $\mu$m (micrometer) in diameter may be used. In other applications, a trench or channel of porous silicon of about 1 μm in width may be used. The size of the porous silicon chamber is not limiting, and it is contemplated that any size or shape of porous silicon chamber may be used. A 1 μm chamber size may be of use, for example, with an excitatory laser that is 1 μm in size.

The exemplary method disclosed above is not limiting for producing porous silicon substrates and it is contemplated that any method known in the art may be used. Non-limiting examples of methods for making porous silicon substrates include anodic etching of silicon wafers; electroplating; and depositing a silicon/oxygen containing material followed by controlled annealing; (e.g., Canham, "Silicon quantum wire array fabrication by electrochemical and chemical dissolution of wafers," Appl. Phys. Lett. 57:1046, 1990; U.S. Pat. Nos. 5,561,304; 6,153,489; 6,171,945; 6,322,895; 6,358,613; 6,358,815; 6,359,276). A porous silicon layer may be attached to one or more supporting layers, such as bulk silicon, quartz, glass and/or plastic. An etch stop layer, such as silicon nitride, may be used to control the depth of etching. The porous silicon layer may be incorporated into a semiconductor chip, using known methods of chip manufacture. The metal-coated porous silicon chamber may be designed as part of an integral chip, connected to various channels, microchannels, nanochannels, microfluidic channels, reaction chambers, etc. Alternatively, the metal-coated porous silicon chamber may be cut out of a silicon wafer and incorporated into a chip and/or other device.

It is contemplated that additional modifications to the porous silicon substrate may be made, either before or after metal coating. For example, after etching a porous silicon substrate may be oxidized, using methods known in the art, to silicon oxide and/or silicon dioxide. Oxidation may be used, for example, to increase the mechanical strength and stability of the porous silicon substrate. Alternatively, the metal-coated silicon substrate may be subjected to further etching to remove the silicon material, leaving a metal shell that may be left hollow or may be filled with other materials, such as additional Raman active metal.

Metal Coating of Porous Silicon

The porous silicon substrate may be coated with a Raman active metal, such as gold, silver, platinum, copper or aluminum, by any method known in the art. Non-limiting exemplary methods include electroplating; cathodic electromigration; evaporation and sputtering of metals; using seed crystals to catalyze plating (i.e. using a copper/nickel seed to plate gold); ion implantation; diffusion; or any other method known in the art for plating thin metal layers on a silicon substrate. (See, e.g., Lopez and Fauchet, "Erbium emission form porous silicon one-dimensional photonic band gap structures," Appl. Phys. Lett. 77:3704–6, 2000; U.S. Pat. Nos. 5,561,304; 6,171,945; 6,359,276.) Another non-limiting example of metal coating comprises electroless plating (e.g., Gole et al., "Patterned metallization of porous silicon from electroless solution for direct electrical contact," J. Electrochem. Soc. 147:3785, 2000). The composition and/or thickness of the metal layer may be controlled to optimize the plasmon resonance frequency of the metal-coated porous silicon.

The Raman active substrate used for analyte detection may comprise a metal-coated, nanocrystalline, porous silicon substrate, immobilized metal colloids, such as silver or gold nanoparticles, coated on a different type of substrate, and/or immobilized metal colloids coated on top of a metal-coated, nanocrystalline, porous silicon substrate. The latter composition would have a very high density of Raman active metal, with relatively small channels for analytes in solution to enter the substrate. Although this may be less favorable for large analyte molecules, such as large proteins or nucleic acids, it may provide better sensitivity and detection of small analytes, such as single nucleotides or amino acids. Metal colloids may be in the form of nanoparticles, as discussed below.

Arsenic-anodized porous silicon is known to function as a moderate reducing agent for metal ions, thereby initiating spontaneous immersion plating of metal on the top surface of the porous area, and closing the pore openings. Thus, using standard methods of metal impregnation, it is difficult to obtain a uniform metal depth profile while maintaining an open porous surface. There is a trade-off between the unblocked pores and metal penetration depth, which can be explained as follows. High concentrations of metal ion are needed to obtain a better metal depth profile. However, exposure to high concentrations of metal salt solutions close the pores due to the thick metal film deposition from the spontaneous immersion plating reaction. To maintain an open pore, the concentration of metal ion in solution needs to be lower. However, this causes poorer penetration depth, as well as reducing the amount of metal deposited. This problem is resolved by the methods disclosed herein, which allow a more uniform metal deposition without pore clogging.

Metal Coating by Thermal Decomposition of a Metal Salt

Figure 4:
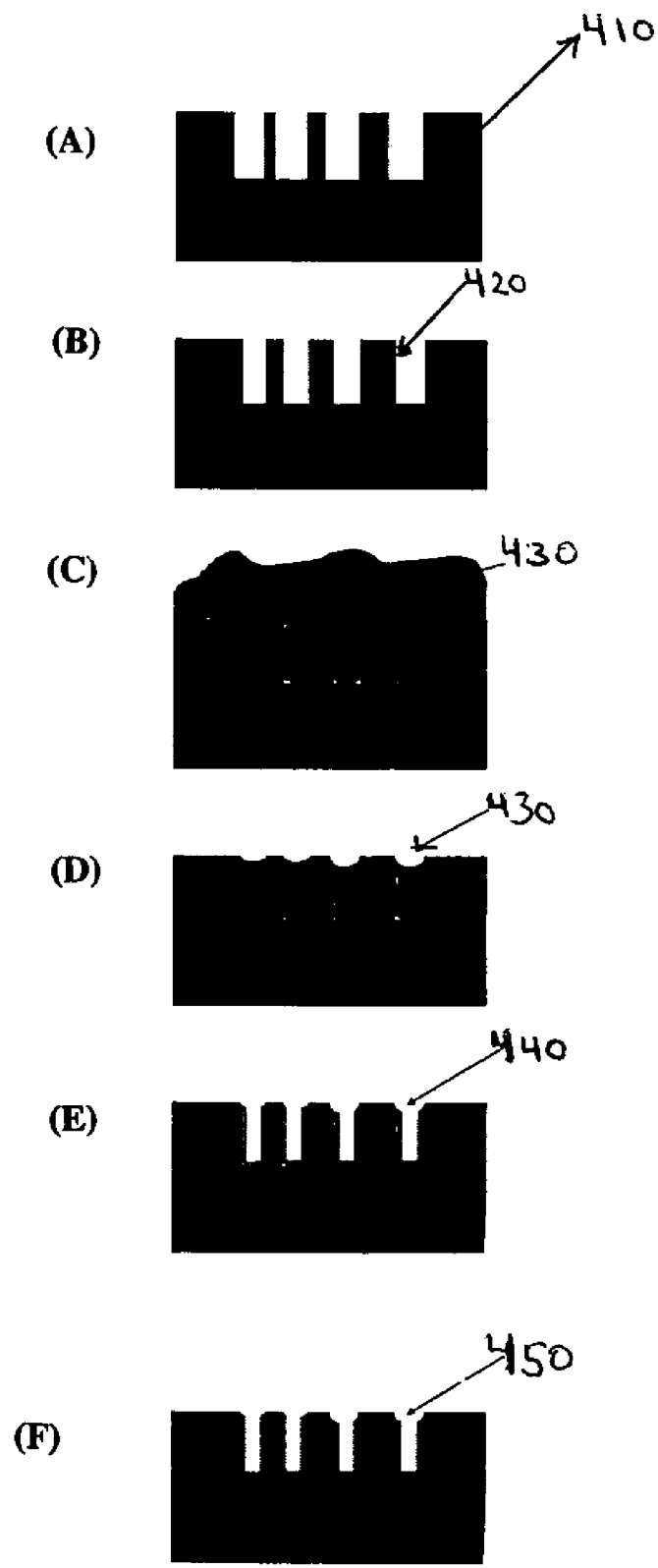
FIG. 4 illustrates an exemplary method for producing a metal-coated porous silicon substrate comprising thermal decomposition of a metal salt solution.

As illustrated in FIG. 4, a porous silicon substrate 410 may be uniformly coated with a metal 450, such as a Raman sensitive metal 450, by a method comprising thermal decomposition of a metal salt layer 440. The metal 450 may be silver, gold or other Raman active metal. A porous silicon substrate 410 (FIG. 4A) may be obtained, for example, as disclosed above. To prevent premature metal 450 deposition and pore blocking, the surface layer of silicon may be oxidized to silicon dioxide 420 (FIG. 4B), for example by chemical oxidation or plasma oxidation. Oxidation prevents spontaneous immersion plating by stabilizing the porous silicon surface 420. In the absence of oxidation, positively charged silver cations can engage in a redox reaction with unoxidized silicon 410, resulting in spontaneous silver metal 450 deposition.

Following oxidation, the porous silicon substrate 410 may be wet with a metal salt solution 430, such as a 1 M solution of silver nitrate ($AgNO_3$) (FIG. 4C). In a non-limiting example, the oxidized porous silicon substrate 410 is dipped into a silver nitrate solution 430 for 20 minutes, until the pores are completely wet with the silver nitrate solution 430. Excess metal salt solution is removed, for example, by nitrogen gun drying (FIG. 4D). The solution 430 remaining in the pores may be dried (FIG. 4E), for example, by heating to 100° C. for 20 min. At this point, the solvent has evaporated and a thin layer of dry silver nitrate salt 440 is deposited on the surface of the porous silicon 410. The dry salt 440 may be thermally decomposed (FIG. 4F), for example by heating to 500° C. for 30 min in an ambient pressure furnace. The reaction of Equation 1 occurs spontaneously at temperatures above 573° K. (about 300° C.). The nitrate ion is converted to gaseous nitrogen dioxide according to Equation 1, resulting in deposition of a uniform layer of metallic silver 450 coating the porous silicon substrate 410 (FIG. 4F). Although nitrogen dioxide has been used as a photoetching agent, under the conditions of the disclosed method it does not etch the silicon dioxide layer 420.

$$AgNO_3 \rightarrow Ag(s) + NO_2(gas) + \tfrac{1}{2}O_2(gas) \qquad (1)$$

The thickness of the deposited metal layer 450 may be controlled, for example, by varying the concentration of the metal salt solution 430. Depending on the thickness of metal layer 450 to be deposited, the salt solution 430 concentration can vary between a wide range, of about 0.1, 0.2, 0.3, 0.4, 0.5, 0.6, 0.7, 0.8, 0.9, 1.0, 1.25, 1.5, 1.75, 2.0, 2.5, 3.0, 3.5, 4.0, 4.5 to 5.0 M (molar). Although the exemplary method utilizes a silver solution 430, the methods are not limited to depositing silver 450 but may encompass any known metal 450, including but not limited to Raman active metals such as gold, copper, platinum, aluminum, etc. The methods are also not limited as to the type of salt used. The anionic species used to form the metal salt may be one that is converted to a gaseous species and driven off during the thermal decomposition process, such as nitrate or sulfate ion. However, in other alternatives any anionic species without limitation may be used.

Metal Coating by Microfluidic Impregnation

In alternative methods, a porous membrane, such as a porous silicon membrane, may be coated with metal using microfluidic impregnation. In an exemplary method, a porous silicon membrane may be obtained as disclosed above. The porous silicon layer may be electropolished and suspended in a solution. The electropolished membrane may be inserted into a microfluidic pathway between one or more solvent reservoirs and a waste reservoir that are connected through cross-paths. Such microfluidic pathways may be produced by any method known in the art, such as micromolding with PDMS (polydimethyl siloxane), standard lithography techniques or photolithography and etching of various chip materials (e.g., Duffy et al., *Anal. Chem.* 70:4974–84, 1998). The porous silicon membrane may be incorporated into any type of microfluidic system. Microfluidic systems incorporating porous silicon membranes may be of use for a wide variety of applications relating to analysis and/or separation of polymer molecules, including but not limited to proteins and nucleic acids. Methods for micro and/or nanoscale manufacturing are known in the art, as discussed in more detail below.

A metal salt solution, such as a silver nitrate solution, may be introduced through the solvent reservoir and allowed to flow through the porous silicon membrane to a waste reservoir. A spontaneous reaction will occur, as indicated in Equation 2.

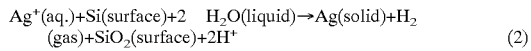

$$Ag^+(aq.)+Si(surface)+2\ H_2O(liquid) \rightarrow Ag(solid)+H_2(gas)+SiO_2(surface)+2H^+ \quad (2)$$

As disclosed in Equation 2, an aqueous metal solution reacts spontaneously with a porous silicon surface in a redox reaction, producing a deposited metal coating on the porous silicon. The thickness of the metal coating may be controlled by the metal salt concentration of the solution, the rate of flow through the microfluidic pathway, the temperature, and/or the length of time that the solution is allowed to flow through the membrane. Techniques for controlling such metal plating reactions are known in the art.

The method is not limited to silver solutions, but may also be performed with solutions of other metal salts, including but not limited to Raman active metals such as gold, platinum, aluminum, copper, etc. In other alternatives, the porous silicon membrane may be coated with two or more different metals, using multiple solvent reservoirs containing different metal plating solutions. One or more reservoirs may contain a wash solution to remove excess metal plating solution. Coating with multiple metals may be used to manipulate the electrical, optical and/or Raman surface characteristics of the metal-coated porous silicon membrane, such as the degree of surface enhancement of the Raman signal, the distance from the surface at which resonance occurs, the range of wavelengths of Raman resonance, etc.

The disclosed methods result in the production of a metal-coated porous silicon membrane integrated into a microfluidic pathway. Such an integrated microchip may be directly incorporated into a Raman detection system. One or more samples suspected of containing target molecules may be loaded into corresponding solvent reservoirs. Samples may be channeled through the microfluidic pathway to enter the metal-coated membrane. Once in the membrane, the target molecule may be excited by an excitatory light source, such as a laser. An emitted Raman signal may be detected by a Raman detector, as discussed in more detail below. Once analyzed, samples may be removed into a waste reservoir, the membrane washed and the next sample analyzed. The Raman detection system may incorporate various components known in the art, such as Raman detectors and excitatory light sources, or may comprise custom components designed to be fully integrated into the system to optimize Raman detection of analytes.

Nanoparticles

Raman active metal particles, such as gold or silver nanoparticles, may be added to the metal-coated porous silicon substrate to further enhance the Raman signal. Nanoparticles of between 1 nm and 2 μm in diameter may be used. Alternatively, nanoparticles of 2 nm to 1 μm, 5 nm to 500 nm, 10 nm to 200 nm, 20 nm to 100 nm, 30 nm to 80 nm, 40 nm to or 50 nm to 60 nm diameter are contemplated. Nanoparticles with an average diameter of 10 to 50 nm, 50 to 100 nm or about 100 nm are also contemplated. The size of the nanoparticles will depend on the diameter of the pores in the metal-coated porous silicon and may be selected so that the nanoparticles fit inside the pores. The nanoparticles may be approximately spherical in shape, although nanoparticles of any shape or of irregular shape may be used. Methods of preparing nanoparticles are known (e.g., U.S. Pat. Nos. 6,054,495; 6,127,120; 6,149,868; Lee and Meisel, *J. Phys. Chem.* 86:3391–3395, 1982). Nanoparticles may also be produced in the form of nanoprisms (Jin et al., "Photoinduced conversion of silver nanospheres to nanoprisms," *Science* 294:1901, 2001). Nanoparticles may be obtained from commercial sources (e.g., Nanoprobes Inc., Yaphank, N.Y.; Polysciences, Inc., Warrington, Pa.).

The nanoparticles may be random aggregates of nanoparticles (colloidal nanoparticles). Alternatively, nanoparticles may be cross-linked to produce particular aggregates of nanoparticles, such as dimers, trimers, tetramers or other aggregates. Heterogeneous mixtures of aggregates of different or homogenous populations of nanoparticle aggregates may be used. Aggregates containing a selected number of nanoparticles (dimers, trimers, etc.) may be enriched or purified by known techniques, such as ultracentrifugation in sucrose gradient solutions.

Methods of cross-linking nanoparticles are known in the art (see, e.g., Feldheim, "Assembly of metal nanoparticle arrays using molecular bridges," The Electrochemical Society Interface, Fall, 2001, pp. 22–25). Reaction of gold nanoparticles with linker compounds bearing terminal thiol or sulfhydryl groups is known (Feldheim, 2001). A single linker compound may be derivatized with thiol groups at both ends. Upon reaction with gold nanoparticles, the linker would form nanoparticle dimers that are separated by the length of the linker. Alternatively, linkers with three, four or more thiol groups may be used to simultaneously attach to multiple nanoparticles (Feldheim, 2001). The use of an excess of nanoparticles to linker compounds prevents formation of multiple cross-links and nanoparticle precipitation. Aggregates of silver nanoparticles may be formed by standard synthesis methods known in the art.

Gold or silver nanoparticles may be coated with derivatized silanes, such as aminosilane, 3-glycidoxypropyltrimethoxysilane (GOP) or aminopropyltrimethoxysilane (APTS). The reactive groups at the ends of the silanes may be used to form cross-linked aggregates of nanoparticles. It is contemplated that the linker compounds used may be of almost any length, ranging from about 0.05, 0.1, 0.2, 0.5, 0.75, 1, 2, 3, 4, 5, 6, 7, 8, 9, 10, 11, 12, 13, 14, 15, 16, 17, 18, 19, 20, 21, 22, 23, 24, 25, 27, 30, 35, 40, 45, 50, 55, 60, 65, 70, 80, 90 to 100 nm or even greater length. Linkers of heterogeneous length may also be used.

The nanoparticles may be modified to contain various reactive groups before they are attached to linker compounds. Modified nanoparticles are commercially available, such as the Nanogold® nanoparticles from Nanoprobes, Inc. (Yaphank, N.Y.). Nanogold® nanoparticles may be obtained with either single or multiple maleimide, amine or other groups attached per nanoparticle. The Nanogold® nanoparticles are also available in either positively or negatively charged form to facilitate manipulation of nanoparticles in an electric field. Such modified nanoparticles may be attached to a variety of known linker compounds to provide dimers, trimers or other aggregates of nanoparticles.

The type of linker compound used is not limiting, so long as it results in the production of small aggregates of nanoparticles that will not precipitate in solution. For example, the linker group may comprise phenylacetylene polymers (Feldheim, 2001). Alternatively, linker groups may comprise polytetrafluoroethylene, polyvinyl pyrrolidone, polystyrene, polypropylene, polyacrylamide, polyethylene or other known polymers. The linker compounds of use are not limited to polymers, but may also include other types of molecules such as silanes, alkanes, derivatized silanes or derivatized alkanes. In particular, linker compounds of relatively simple chemical structure, such as alkanes or silanes, may be used to avoid interfering with the Raman signals emitted by analytes Micro-Electro-Mechanical Systems (MEMS)

The Raman active metal-coated porous silicon substrate may be incorporated into a larger apparatus and/or system. For example, the substrate may be incorporated into a micro-electro-mechanical system (MEMS). MEMS are integrated systems comprising mechanical elements, sensors, actuators, and electronics. All of those components may be manufactured by known microfabrication techniques on a common chip, comprising a silicon-based or equivalent substrate (e.g., Voldman et al., *Ann. Rev. Biomed. Eng.* 1:401–425, 1999). The sensor components of MEMS may be used to measure mechanical, thermal, biological, chemical, optical and/or magnetic phenomena. The electronics may process the information from the sensors and control actuator components such pumps, valves, heaters, coolers, filters, etc. thereby controlling the function of the MEMS.

The electronic components of MEMS may be fabricated using integrated circuit (IC) processes (e.g., CMOS, Bipolar, or BICMOS processes). They may be patterned using photolithographic and etching methods known for computer chip manufacture. The micromechanical components may be fabricated using compatible "micromachining" processes that selectively etch away parts of the silicon wafer or add new structural layers to form the mechanical and/or electromechanical components.

Basic techniques in MEMS manufacture include depositing thin films of material on a substrate, applying a patterned mask on top of the films by photolithographic imaging or other known lithographic methods, and selectively etching the films. A thin film may have a thickness in the range of a few nanometers to 100 micrometers. Deposition techniques of use may include chemical procedures such as chemical vapor deposition (CVD), electrodeposition, epitaxy and thermal oxidation and physical procedures like physical vapor deposition (PVD) and casting. Methods for manufacture of nanoelectromechanical systems may be used for certain embodiments of the invention. (See, e.g., Craighead, Science 290:1532–36,2000.)

The metal-coated porous silicon substrate may be connected to various fluid filled compartments, such as microfluidic channels, nanochannels and/or microchannels. These and other components of the apparatus may be formed as a single unit, for example in the form of a chip as known in semiconductor chips and/or microcapillary or microfluidic chips. Alternatively, the metal-coated porous silicon substrate may be removed from a silicon wafer and attached to other components of an apparatus. Any materials known for use in such chips may be used in the disclosed apparatus, including silicon, silicon dioxide, silicon nitride, polydimethyl siloxane (PDMS), polymethylmethacrylate (PMMA), plastic, glass, quartz, etc.

Techniques for batch fabrication of chips are well known in the fields of computer chip manufacture and/or microcapillary chip manufacture. Such chips may be manufactured by any method known in the art, such as by photolithography and etching, laser ablation, injection molding, casting, molecular beam epitaxy, dip-pen nanolithography, chemical vapor deposition (CVD) fabrication, electron beam or focused ion beam technology or imprinting techniques. Non-limiting examples include conventional molding with a flowable, optically clear material such as plastic or glass; photolithography and dry etching of silicon dioxide; electron beam lithography using polymethylmethacrylate resist to pattern an aluminum mask on a silicon dioxide substrate, followed by reactive ion etching. Methods for manufacture of nanoelectromechanical systems may be used for certain embodiments of the invention. (See, e.g., Craighead, Science 290:1532–36, 2000.) Various forms of microfabricated chips are commercially available from, e.g., Caliper Technologies Inc. (Mountain View, Calif.) and ACLARA BioSciences Inc. (Mountain View, Calif.).

Part or all of an apparatus may be selected to be transparent to electromagnetic radiation at the excitation and emission frequencies used for Raman spectroscopy, such as glass, silicon, quartz or any other optically clear material. For fluid-filled compartments that may be exposed to various biomolecules, such as proteins, peptides, nucleic acids, nucleotides and the like, the surfaces exposed to such molecules may be modified by coating, for example to transform a surface from a hydrophobic to a hydrophilic surface and/or to decrease adsorption of molecules to a surface. Surface modification of common chip materials such as glass, silicon, quartz and/or PDMS is known in the art (e.g., U.S. Pat. No. 6,263,286). Such modifications may include, but are not limited to, coating with commercially available capillary coatings (Supelco, Bellafonte, Pa.), silanes with various functional groups such as polyethyleneoxide or acrylamide, or any other coating known in the art.

Raman Spectroscopy

The disclosed methods, systems and apparatus may be used for the detection and/or identification of analytes by surface enhanced Raman spectroscopy (SERS), surface enhanced resonance Raman spectroscopy (SERRS) and/or coherent anti-Stokes Raman spectroscopy (CARS) detection. Compared to existing techniques, the disclosed methods, systems and apparatus provide SERS active substrates with increased and more uniform metal density and greater depth of field of SERS enhancement, allowing more efficient Raman detection and/or identification of analytes.

Previous methods for SERS detection of various analytes have used colloidal metal particles, such as aggregated silver nanoparticles, that were typically coated onto a substrate and/or support (e.g., U.S. Pat. Nos. 5,306,403; 6,149,868; 6,174,677; 6,376,177). While such arrangements occasionally allow SERS detection with as much as $10^6$ to $10^8$ increased sensitivity, they are not capable of single molecule detection of small analytes such as nucleotides, as disclosed herein. Enhanced sensitivity of Raman detection is apparently not uniform within a colloidal particle aggregate, but rather depends on the presence of "hot spots." The physical structure of such hot spots, the range of distances from the metal nanoparticles at which enhanced sensitivity occurs, and the spatial relationships between aggregated nanoparticles and analytes that allow enhanced sensitivity have not been characterized. Further, aggregated metal nanoparticles may be unstable in solution, with adverse effects on the reproducibility of single molecule detection. The present methods, systems and apparatus provide a stable microenvironment for SERS detection in which the physical conformation and density of the Raman-active metal porous substrate may be precisely controlled, allowing reproducible, sensitive and accurate detection of analytes in solution.

Raman Detectors

Analytes may be detected and/or identified by any known method of Raman spectroscopy. The Raman active substrate may be operably coupled to one or more Raman detection units. Various methods for detection of analytes by Raman spectroscopy are known in the art. (See, e.g., U.S. Pat. Nos. 6,002,471; 6,040,191; 6,149,868; 6,174,677; 6,313,914). Variations on surface enhanced Raman spectroscopy (SERS), surface enhanced resonance Raman spectroscopy (SERRS), hyper-Raman spectroscopy and coherent anti-Stokes Raman spectroscopy (CARS) have been disclosed. In SERS and SERRS, the sensitivity of the Raman detection is enhanced by a factor of $10^6$ or more for molecules adsorbed on roughened metal surfaces, such as silver, gold, platinum, copper or aluminum surfaces.

A non-limiting example of a Raman detection unit is disclosed in U.S. Pat. No. 6,002,471. An excitation beam is generated by either a frequency doubled Nd:YAG laser at 532 nm wavelength or a frequency doubled Ti:sapphire laser at 365 nm wavelength. Pulsed laser beams or continuous laser beams may be used. The excitation beam passes through confocal optics and a microscope objective, and is focused onto the Raman active substrate containing one or more analytes. The Raman emission light from the analytes is collected by the microscope objective and the confocal optics and is coupled to a monochromator for spectral dissociation. The confocal optics includes a combination of dichroic filters, barrier filters, confocal pinholes, lenses, and mirrors for reducing the background signal. Standard full field optics can be used as well as confocal optics. The Raman emission signal is detected by a Raman detector, comprising an avalanche photodiode interfaced with a computer for counting and digitization of the signal.

Another example of a Raman detection unit is disclosed in U.S. Pat. No. 5,306,403, including a Spex Model 1403 double-grating spectrophotometer with a gallium-arsenide photomultiplier tube (RCA Model C31034 or Burle Industries Model C3103402) operated in the single-photon counting mode. The excitation source comprises a 514.5 nm line argon-ion laser from SpectraPhysics, Model 166, and a 647.1 nm line of a krypton-ion laser (Innova 70, Coherent).

Alternative excitation sources include a nitrogen laser (Laser Science Inc.) at 337 nm and a helium-cadmium laser (Liconox) at 325 nm (U.S. Pat. No. 6,174,677), a light emitting diode, an Nd:YLF laser, and/or various ions lasers and/or dye lasers. The excitation beam may be spectrally purified with a bandpass filter (Corion) and may be focused on the Raman active substrate using a 6× objective lens (Newport, Model L6x). The objective lens may be used to both excite the analytes and to collect the Raman signal, by using a holographic beam splitter (Kaiser Optical Systems, Inc., Model HB 647-26N18) to produce a right-angle geometry for the excitation beam and the emitted Raman signal. A holographic notch filter (Kaiser Optical Systems, Inc.) may be used to reduce Rayleigh scattered radiation. Alternative Raman detectors include an ISA HR-320 spectrograph equipped with a red-enhanced intensified charge-coupled device (RE-ICCD) detection system (Princeton Instruments). Other types of detectors may be used, such as Fourier-transform spectrographs (based on Michaelson interferometers), charged injection devices, photodiode arrays, InGaAs detectors, electron-multiplied CCD, intensified CCD and/or phototransistor arrays.

Any suitable form or configuration of Raman spectroscopy or related techniques known in the art may be used for detection of analytes, including but not limited to normal Raman scattering, resonance Raman scattering, surface enhanced Raman scattering, surface enhanced resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy.

Raman Labels

Certain methods may involve attaching a label to one or more analytes to facilitate their measurement by the Raman detection unit. Non-limiting examples of labels that could be used for Raman spectroscopy include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins, aminoacridine, quantum dots, carbon nanotubes and fullerenes. These and other Raman labels may be obtained from commercial sources (e.g., Molecular Probes, Eugene, Oreg.; Sigma Aldrich Chemical Co., St. Louis, Mo.) and/or synthesized by methods known in the art.

Polycyclic aromatic compounds may function as Raman labels, as is known in the art. Other labels that may be of use for particular embodiments of the invention include cyanide, thiol, chlorine, bromine, methyl, phosphorus and sulfur. The use of labels in Raman spectroscopy is known (e.g., U.S. Pat. Nos. 5,306,403 and 6,174,677). The skilled artisan will realize that the Raman labels used should generate distinguishable Raman spectra and may be specifically bound to or associated with different types of analytes.

Labels may be attached directly to the analytes or may be attached via various linker compounds. Cross-linking reagents and linker compounds of use in the disclosed methods are known in the art. Raman labels that contain reactive groups designed to covalently react with other molecules, such as analytes, are commercially available (e.g., Molecular Probes, Eugene, Oreg.). Methods for preparing labeled analytes are known (e.g., U.S. Pat. Nos. 4,962,037; 5,405,747; 6,136,543; 6,210,896).

EXAMPLES

Example 1

Construction of a Raman Active Substrate

Formation of Porous Nanocrystalline Silicon

An exemplary method and apparatus 100 for forming nanocrystalline porous silicon substrates 110 is illustrated in FIG. 1. Methods for making nanocrystalline porous silicon are known in the art (e.g., U.S. Pat. No. 6,017,773). A layer of nanocrystalline porous silicon may be formed electrochemically as disclosed in Petrova-Koch et al. (Appl. Phys. Let. 61:943, 1992). Depending on the particular application, the silicon may be lightly or heavily p-doped or n-doped prior to etching to regulate the characteristics of the porous silicon substrate 110. Single crystal silicon ingots may be fabricated by the well known Czochralski method (e.g., http://www.msil.ab.psiweb.com/english/msilhist4-e.html). A single crystal silicon wafer 110 may be treated with anodic etching in dilute HF/ethanol 150 to form a nanocrystalline porous silicon substrate 110. Alternatively, chemical etching in a solution of HF, nitric acid and water 150 may be used without anodic etching.

The wafer may be coated with polymethyl-methacrylate resist or any other known resist compound before etching. A pattern for the nanocrystalline porous silicon substrate 110 may be formed by standard photolithographic techniques. The nanocrystalline porous substrate 110 may be circular, trench shaped, channel shaped or of any other selected shape. Multiple porous substrates 110 may be formed on a single silicon wafer 110 to allow for multiple sampling channels and/or chambers for Raman analysis. Each sampling channel and/or chamber may be operably coupled to one or more Raman detectors.

After resist coating and lithography, the wafer 110 may be exposed to a solution of between about 15 to 50 weight percent HF 150 in ethanol and/or distilled water in an electrochemical cell 120 comprised of Teflon®, as disclosed in FIG. 1. The entire resist coated wafer 110 may be immersed in an HF 150 solution. Alternatively, the wafer 110 may be held in place in the electrochemical cell 120, for example using a synthetic rubber washer, with only a portion of the wafer 110 surface exposed to the HF 150 solution (U.S. Pat. No. 6,322,895). In either case, the wafer 110 may be electrically connected to the positive pole of a constant current source 130 to form the anode 110 of the electrochemical cell 120. A platinum electrode may provide the cathode 140 for the cell 120. The wafer 110 may be etched using an anodization current density of between 5 to 250 milliamperes/cm$^2$ for between 5 seconds to 30 minutes in the dark, depending on the selected degree of porosity. In particular embodiments of the invention, a porosity of about 10%, 15%, 20%, 25%, 30%, 35%, 40%, 45%, 50%, 60%, 70%, 80% or 90% may be selected. As is known in the art, the anodization current density required to form porous silicon 110 may depend in part on the type of silicon substrate 110 used, such as whether the substrate 110 is lightly or heavily p-doped or n-doped.

The nanocrystalline porous silicon substrate 110 may be incorporated into a MEMS device comprising a variety of detectors, sensors, electrodes, other electrical components, mechanical actuators, etc. using known chip manufacturing techniques. Such manufacturing procedures may occur before and/or after formation of the porous silicon substrate 110 and/or coating with a Raman sensitive metal.

Metal Coating

Figure 2:
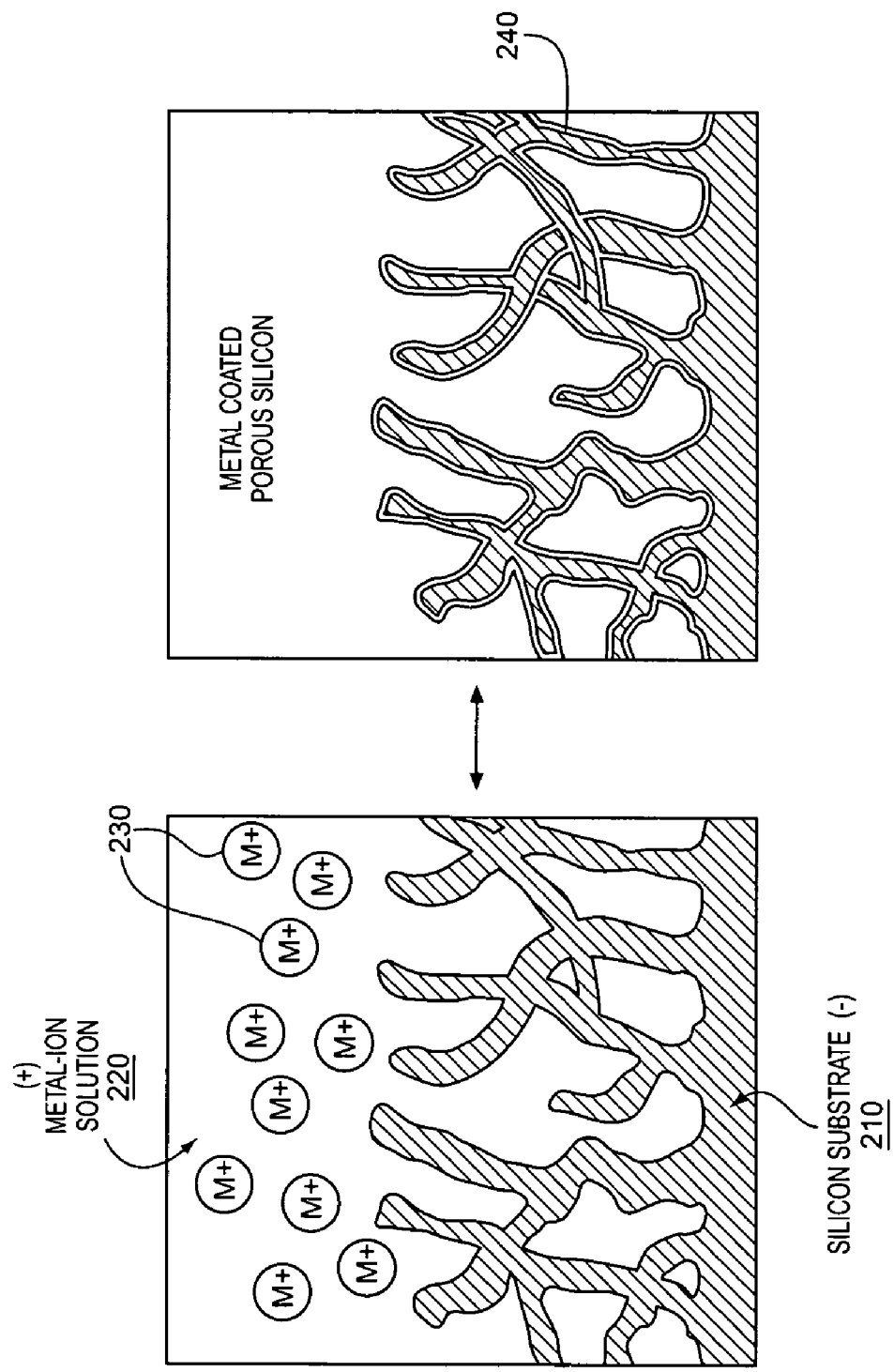
FIG. 2 illustrates an exemplary method for producing a metal-coated porous silicon substrate 240.

As illustrated in FIG. 2, the porous silicon 210 may be coated with metal 240 by cathodic electromigration using known techniques (Lopez and Fauchet, 2000). For the purposes of the present Example, silver is used for the metal coating 240, although other metals 240 such as gold or platinum may be used. The porous silicon surface 210 is cleaned and doped with silver 240 by electromigration according to Lopez and Fauchet (Appl. Phys. Lett. 75:3989, 1999). The porous silicon substrate 210 is exposed to a metal ion solution 220 comprising silver cations 230. The skilled artisan will realize that any known technique for forming a thin metal coat 240 on a porous silicon substrate 210 may be used.

Example 2

Metal Coating of Porous Silicon by Thermal Decomposition

FIG. 4 illustrates an exemplary method for uniformly impregnating metal 450 into nanoporous silicon. The surface of the porous silicon is oxidized to silicon dioxide (FIG. 4B). A metal salt solution is diffused into the porous matrix (FIG. 4C) and dried (FIG. 4E). The dried metal salt is thermally decomposed inside the pores to form a uniform metal layer (FIG. 4F). Oxidation of the porous silicon surface enables complete wetting of porous silicon in the metal salt solution, while preventing spontaneous immersion coating, which causes pore blockage. The dry metal salt is thermally decomposed in a furnace and pure metal is deposited on the side walls of the nanopores. A uniform, thin metal coating of nanoporous silicon may be obtained without plugging the pores, as often observed with standard methods of metal infiltration into nanoporous silicon. Currently available plating methods are also diffusion limited, resulting in non-uniform metal deposition that can decrease the reproducibility of analyte detection, depending upon where in the metal-coated substrate the analyte is located.

An optimal immersion time and high metal ion concentration are needed to make the metal coat the entire porous structure. These requirements can be satisfied by oxidizing the surface of porous silicon, either by chemical oxidation or plasma oxidation, prior to exposure to a metal salt solution (FIG. 4B). Oxidation prevents spontaneous immersion plating by stabilizing the porous surface. The oxidized porous silicon may thus be immersed in highly concentrated metal salt solution without causing pore blockage (FIG. 4C). Excessive metal salt solution may be removed, for example by blowing nitrogen gas (FIG. 4D). The solvent is evaporated to increase absorption of metal salt on the porous surface (FIG. 4E). The metal salts are thermally decomposed (FIG. 4F) to form a uniform deposit of Raman active metal on the surface of the porous silicon substrate.

In a non-limiting example a porous silicon substrate was formed by electrochemical etching in a 15% HF solution, exposing boron doped crystalline silicon to a current density of 50 mA/cm$^2$. The porous silicon substrate was subjected to plasma oxidation in a Technics oxygen plasma chamber at an oxygen flow rate of 50 sccm (standard cubic centimeters) and radiofrequency power of 300 W (watts) for 20 min, resulting in formation of an approximately 50 Å (Angstrom) silicon dioxide layer on the surface of the pores. Alternatively, chemical oxidation in piranha solution may be used (e.g., http://www-device.eecs.Berkeley.edu/-daewon/labweek7.pdf). The silicon dioxide layer passivates the silicon dangling bond, preventing fast immersion coating.

The oxidized porous silicon was dipped in a 1 M $AgNO_3$ solution for 20 min at room temperature to completely wet the pores with silver nitrate solution. Excessive silver nitrate solution was removed by nitrogen gun drying to prevent pore closure by excessive silver deposition. The solvent was removed from the remaining silver nitrate solution by drying at 100° C. for 20 min. At this stage all the solvent was evaporated and dry silver nitrate salt was absorbed on the surface of pores, resulting in an observable brown color on the surface of the porous silicon.

Figure 5:
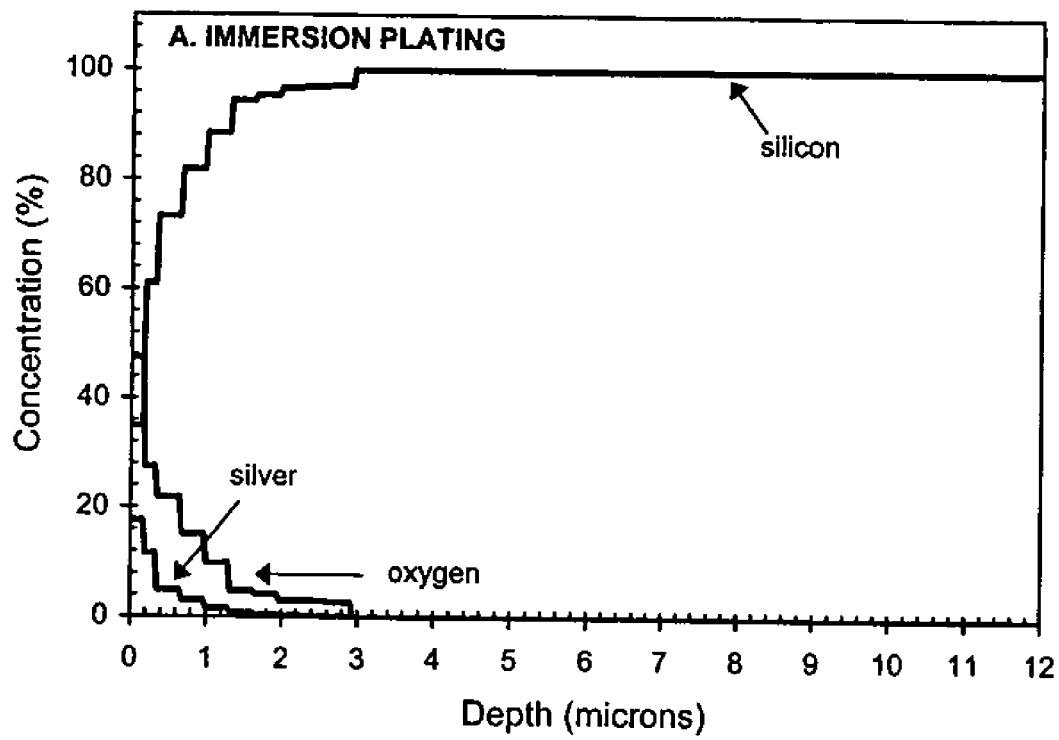
FIG. 5 illustrates the uniform deposition of an exemplary metal (silver) on a porous silicon substrate obtained using a thermal decomposition method. (A) Silver depth profile for nanoporous silicon treated by conventional diffusion limited immersion plating. (B) Silver depth profile for a plasma-oxidized, dip and decomposed (PODD) porous silicon substrate uniformly coated with silver.
Figure 5:
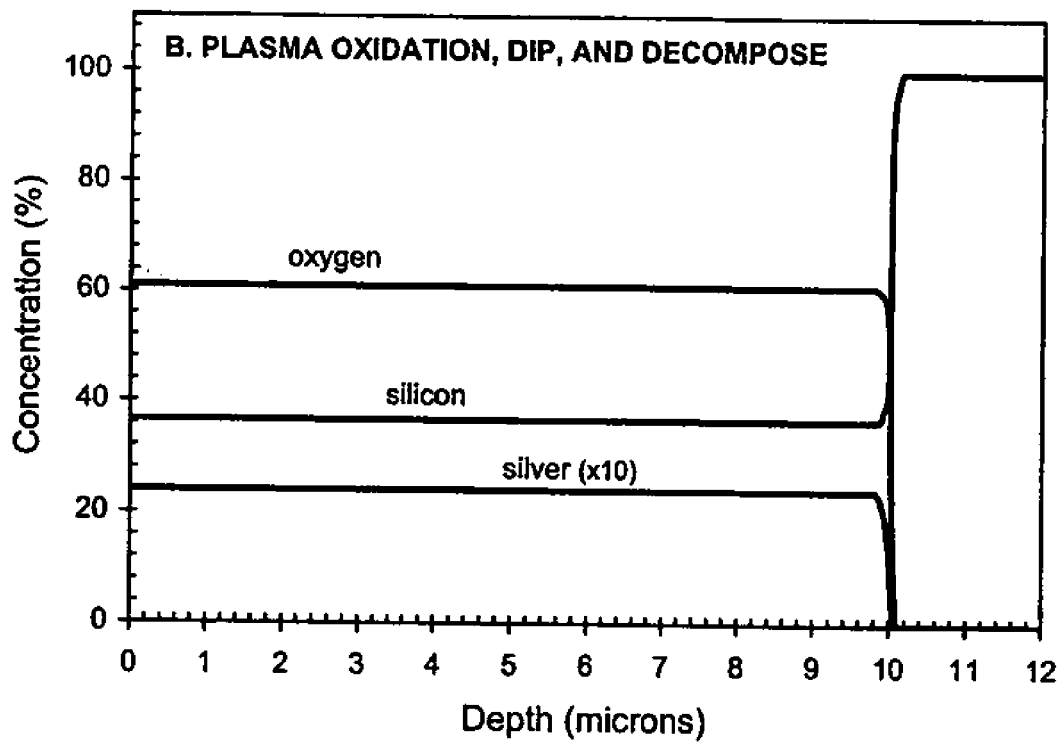

Thermal decomposition was performed for 30 min at 500° C. in an ambient pressure furnace, resulting in the decomposition of the dry silver nitrate salt to silver metal. The method disclosed herein resulted in the formation of a highly uniform deposit of silver metal on the surface of the porous silicon substrate, as shown in FIG. 5. FIG. 5 illustrates the silver depth profile obtained on nanoporous silicon, as determined by Rutherford backscattering spectroscopy analysis. The silver depth profile was compared for nanoporous silicon treated by conventional diffusion limited immersion plating in a 1 mM $AgNO_3$ solution for 2.5 min (FIG. 5A) versus the method of the present Example (FIG. 5B). As can be seen, the present method resulted in a highly uniform silver deposit, of much greater penetration depth compared to the standard method (FIG. 5A and FIG. 5B). The present method resulted in a uniform silver deposit up to about 10 $\mu$m in depth (FIG. 5B), while the standard method resulted in a highly non-uniform deposit of less than 3 $\mu$m in depth (FIG. 5A). The Rutherford backscattering data were corrected using scanning electron microscopy analysis to determine the actual thickness of the porous silicon layer.

Comparing the distribution of silver versus silicon using the present method (FIG. 5B), it is observed that the silver deposition is uniform down to the level at which the silicon density reaches a maximum. That is, the data of FIG. 5B indicate that the metal deposit obtained with the present method extends homogeneously all the way to the bottom of the pores in the porous silicon substrate. It is clear that using the standard method (FIG. 5A) the metal deposit ends well before the bottom of the pores.

Example 3

Raman Detection of Analytes

Figure 3:
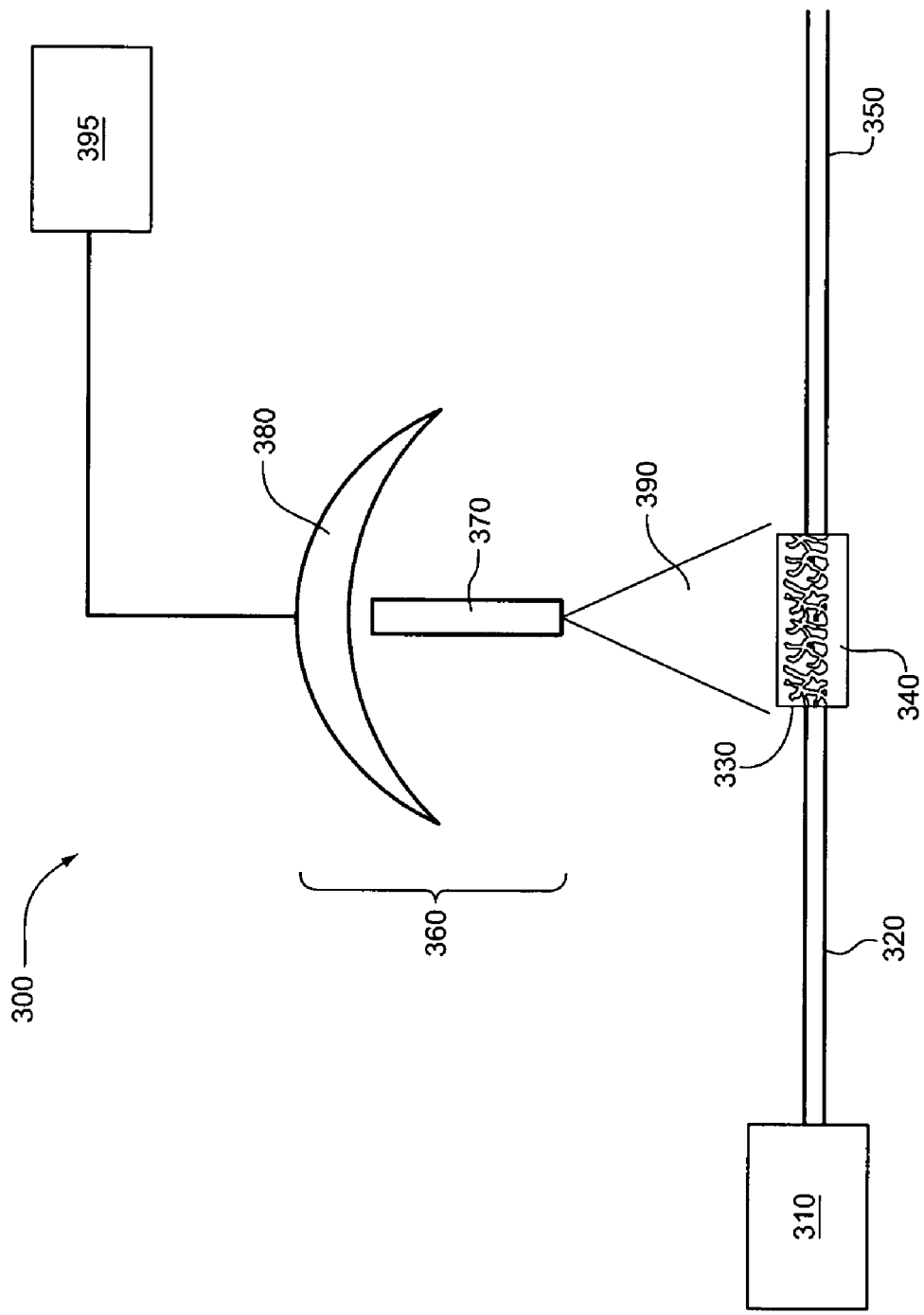
FIG. 3 illustrates an exemplary apparatus 300 and method for detecting and/or identifying analytes using a metal-coated SERS-active substrate 340.

As exemplified in FIG. 3, a Raman active metal-coated substrate 340 formed as disclosed above may be incorporated into an apparatus 300 for Raman detection, identification and/or quantification of analytes. The substrate 340 may be incorporated into, for example, a flow through cell 330, connected to inlet 320 and outlet 350 channels. The inlet channel 320 may be connected to one or more other devices 310, such as a sample injector 310 and/or reaction chamber 310. Analytes may enter the flow through cell 330 and pass across the Raman active substrate 340, where they may be detected by a Raman detection unit 360. The detection unit 360 may comprise a Raman detector 380 and a light source 370, such as a laser 370. The laser 370 may emit an excitation beam 390, activating the analytes and resulting in emission of Raman signals. The Raman signals are detected by the detector 380. In certain embodiments of the invention, the detector 380 may be operably coupled to a computer 395 which can process, analyze, store and/or transmit data on analytes present in the sample.

In an exemplary embodiment of the invention, the excitation beam 390 was generated by a titanium:sapphire laser 370 (Tsunami by Spectra-Physics) at a near-infrared wavelength (750–950 nm) or a galium aluminum arsenide diode laser 370 (PI-ECL series by Process Instruments) at 785 nm or 830 nm. Pulsed laser beams 390 or continuous beams 390 were used. The excitation beam 390 was transmitted through a dichroic mirror (holographic notch filter by Kaiser Optical or an interference filter by Chroma or Omega Optical) into a collinear geometry with the collected beam. The transmitted beam 390 passed through a microscope objective (Nikon LU series), and was focused onto the Raman active substrate 240, 340 where target analytes were located. The Raman scattered light from the analytes was collected by the same microscope objective, and passed the dichroic mirror to the Raman detector 380. The Raman detector 380 comprised a focusing lens, a spectrograph, and an array detector. The focusing lens focused the Raman scattered light through the entrance slit of the spectrograph. The spectrograph (Acton Research) comprised a grating that dispersed the light by its wavelength. The dispersed light was imaged onto an array detector (back-illuminated deep-depletion CCD camera by RoperScientific). The array detector was connected to a controller circuit, which was connected to a computer 395 for data transfer and control of the detector 380 function. Exemplary Raman spectra are disclosed in Example 5 below.

The detection unit 360 may be capable of detecting, identifying and/or quantifying a wide variety of analytes with high sensitivity, down to single molecule detection and/or identification. The analytes may comprise single nucleotides that may or may not be Raman labeled. One or more oligonucleotide probes may or may not be labeled with distinguishable Raman labels and allowed to hybridize to target nucleic acids in a sample. The presence of a target nucleic acid may be indicated by hybridization with a complementary oligonucleotide probe and Raman detection using the apparatus 300 of FIG. 3. Alternatively, amino acids, peptides and/or proteins of interest may be detected and/or identified using the disclosed methods and apparatus 300. The skilled artisan will realize that the methods and apparatus 300 are not limiting as to the type of analytes that may be detected, identified and/or quantified, but rather that any analyte, whether labeled or unlabeled, that can be detected by Raman detection may be analyzed within the scope of the claimed subject matter.

One or more "capture" molecules may be attached either covalently or non-covalently to the Raman active substrate 240, 340 to enhance the sensitivity and/or specificity of Raman detection of analytes. For example, an oligonucleotide probe specific for a selected target nucleic acid could be attached to the metal surface of the substrate 240, 340 by known techniques. (E.g., an oligonucleotide may be covalently modified to contain a sulfhydryl moiety that can bond to a gold-coated substrate 240, 340.) Alternatively, an antibody specific for a target protein, peptide or other compound could be attached to the substrate 240, 340. The presence of a target analyte may be detected by exposing the oligonucleotide attached to the substrate 240, 340 to a sample under conditions allowing for hybridization to complementary nucleic acid sequences, followed by washing and then detection of bound analytes. In alternative embodiments of the invention, one or more analytes in a sample may be labeled with a distinguishable Raman label before exposure to the Raman active substrate 240, 340 to facilitate detection of bound analyte. Similar methods could be used with antibody-antigen pairs, ligand-receptor pairs or any other known pairs of analytes that exhibit selective and/or specific binding to each other. The substrate 240, 340 may be recycled and reused by treatment with various agents to remove bound analytes and/or capture molecules, such as washing with acid, water, organic solvent or detergent, chemical treatment and/or treatment with lytic enzymes such as exonucleases and/or proteases.

Example 4

Detection of Rhodamine 6G (R6G) by SERS

Figure 6:
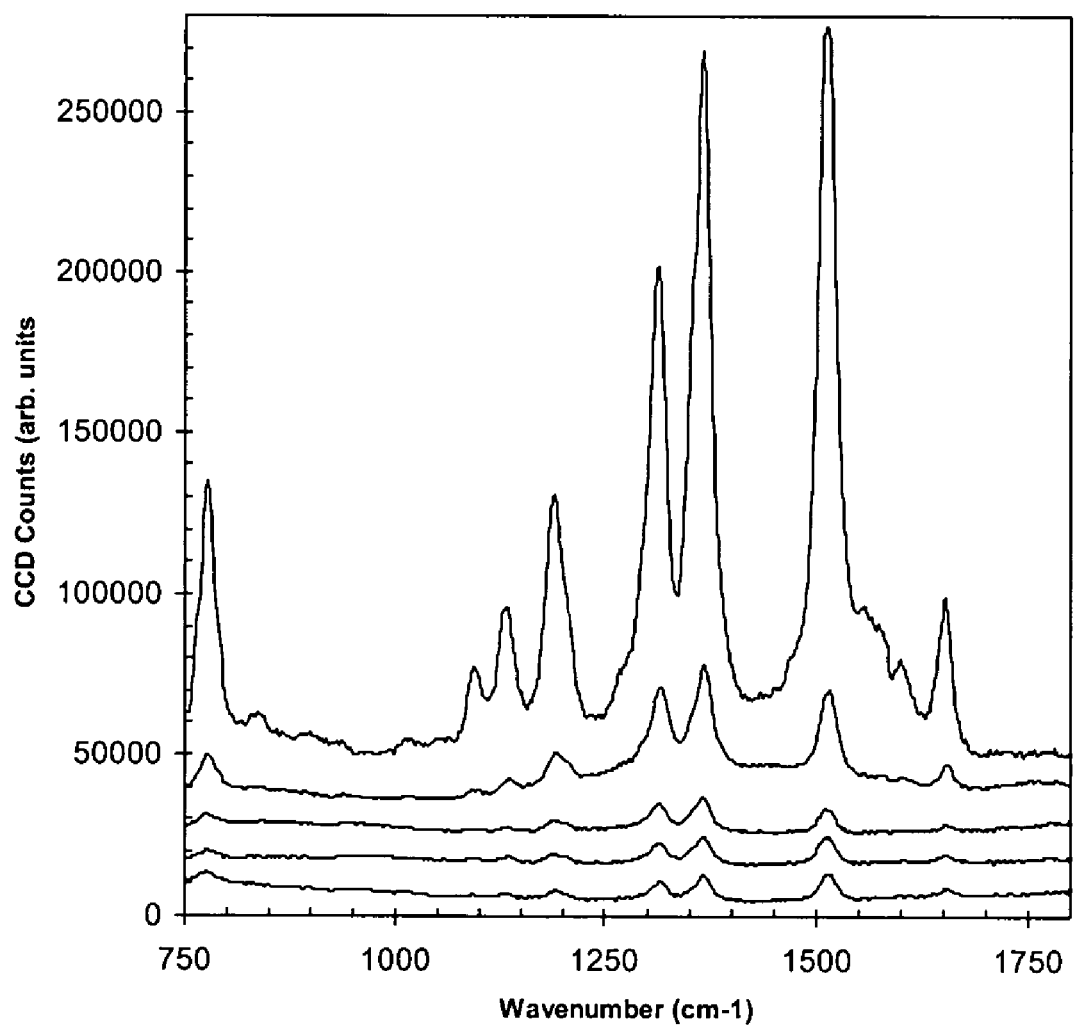
FIG. 6 shows the surface-enhanced Raman spectrum for an exemplary analyte, rhodamine 6G (R6G) dye molecules, obtained with a plasma-oxidized, dip and decomposed (PODD) porous silicon substrate uniformly coated with silver. The PODD substrate was prepared by the method of FIG. 4. A solution of 114 $\mu$M (micromolar) R6G molecules was subjected to SERS (surface enhanced Raman spectroscopy) using excitation at 785 nm (nanometers).

FIG. 6 illustrates the use of the disclosed methods, systems and apparatus for detection and identification of an exemplary analyte, rhodamine 6G (R6G) dye molecules. R6G is a well-characterized dye molecule that may be obtained from standard commercial sources, such as Molecular Probes (Eugene, Oreg.). A 114 $\mu$M (micromolar) solution of R6G was prepared and analyzed by surface enhanced Raman spectroscopy (SERS), using a plasma-oxidized, dip and decomposed (PODD) silver-coated porous silicon substrate that was prepared by the method of Examples 1 and 2. Porous silicon substrates of varying degrees of average porosity were prepared by varying the etching conditions. The R6G solution was diffused into the PODD silver-coated substrate and analyzed by SERS, according to the method of Example 3, using an excitation wavelength of 785 nm. A chemical enhancer (lithium chloride or sodium bromide, about 1 $\mu$M concentration) was added to enhance the Raman signal.

The resulting SERS emission spectra, obtained in PODD silver-coated porous substrates of varying porosity, are shown in FIG. 6. FIG. 6 shows SERS emission spectra for 114 $\mu$m R6G obtained at average porosities, in order from the lowest trace to the highest trace, of 52%, 55%, 65%, 70% and 77%. As indicated in FIG. 6, the intensity of the SERS emission peaks increases with increasing average porosity in this range, with a highest intensity observed at 77% average porosity. Increasing the porosity above 77% pushes the porous silicon layer into a non-stable materials regime, which can result in physical separation of the porous layer from the bulk silicon substrate. At 77% porosity, scanning electron micrographs showed pore diameters of about 32 nm in width (not shown).

At 77% average porosity, a seven order of magnitude ($10^7$) increase in intensity of the Raman emission spectrum was observed. This compares with an approximately six order of magnitude enhancement observed on a roughened silver plate (not shown). Although the intensity of the SERS emission peaks increased as a function of average porosity, the wavelengths of the emission peaks did not vary (FIG. 6), allowing the identification of R6G independent of the average porosity used. With an estimated detection volume of $1.25 \times 10^{-16}$ liters, the corresponding number of molecules of rhodamine 6G detected was approximately 9 molecules.

Figure 7:
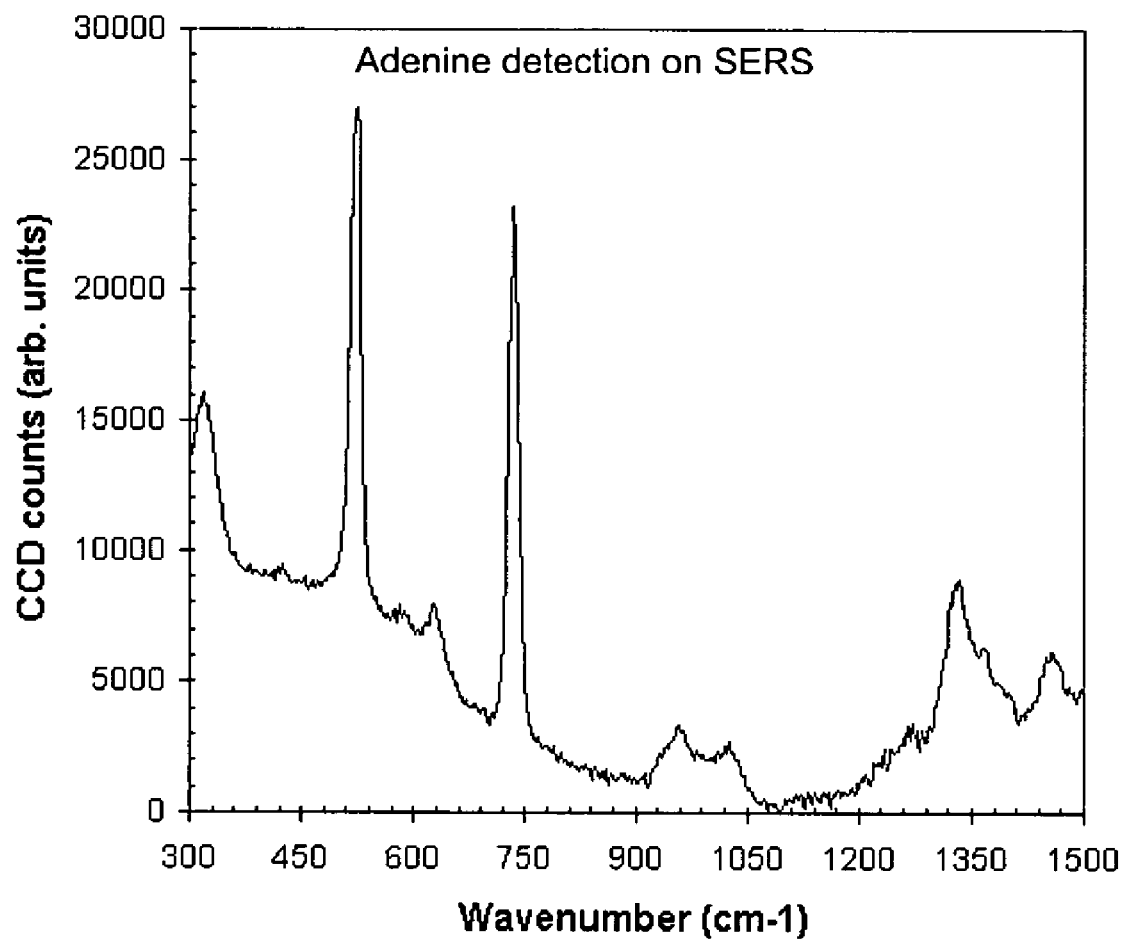
FIG. 7 shows the SERS detection of a 90 $\mu$M solution of adenine using a metal coated nanoporous silicon substrate, made by the method of FIG. 4.

Additional studies were performed with a solution of adenine, which is a more biologically relevant target molecule. Unique spectroscopic features were detected from a 90 $\mu$M solution of adenine on a porous silicon substrate coated with silver (FIG. 7).

Example 5

Raman Detection of Nucleotides

Methods and Apparatus

Raman spectroscopy was performed as disclosed in Example 3 above. For surface-enhanced Raman spectroscopy (SERS), the Raman active substrate consisted of metallic nanoparticles or metal-coated nanostructures. Silver nanoparticles, ranging in size from 5 to 200 nm, was made by the method of Lee and Meisel (*J. Phys. Chem.*, 86:3391, 1982). Alternatively, samples were placed on an aluminum substrate under the microscope objective. The Figures discussed below were collected in a stationary sample on the aluminum substrate. The number of molecules detected was determined by the optical collection volume of the illuminated sample.

Single nucleotides may also be detected by SERS using microfluidic channels. In various embodiments of the invention, nucleotides may be delivered to a Raman active substrate through a microfluidic channel (between about 5 and 200 $\mu$m wide). Microfluidic channels can be made by molding polydimethylsiloxane (PDMS), using the technique disclosed in Anderson et al. ("Fabrication of topologically complex three-dimensional microfluidic systems in PDMS by rapid prototyping," *Anal. Chem.* 72:3158–3164, 2000).

Where SERS was performed in the presence of silver nanoparticles, the nucleotide, purine or pyrimidine analyte was mixed with LiCl (90 $\mu$M final concentration) and nanoparticles (0.25 M final concentration silver atoms). SERS data were collected using room temperature analyte solutions.

Results

Nucleoside monophosphates, purines and pyrimidines were analyzed by SERS, using the system disclosed above. Table 1 shows exemplary detection limits for various analytes of interest.

TABLE 1

SERS Detection of Nucleoside Monophosphates, Purines and Pyrimidines

| Analyte | Final Concentration | Number of Molecules Detected |
| --- | --- | --- |
| dAMP | 9 picomolar (pM) | ~1 molecule |
| Adenine | 9 pM | ~1 molecule |
| dGMP | 90 $\mu$M | $6 \times 10^6$ |
| Guanine | 909 pM | 60 |
| dCMP | 909 $\mu$M | $6 \times 10^7$ |
| Cyotosine | 90 nM | $6 \times 10^3$ |
| dTMP | 9 $\mu$M | $6 \times 10^5$ |
| Thymine | 90 nM | $6 \times 10^3$ |

Conditions were optimized for adenine nucleotides only. LiCL (90 $\mu$M final concentration) was determined to provide optimal SERS detection of adenine nucleotides. Detection of other nucleotides may be facilitated by use of other alkali-metal halide salts, such as NaCl, KCl, RbCl or CsCl. The claimed methods are not limited by the electrolyte solution used, and it is contemplated that other types of electrolyte solutions, such as MgCl, CaCl, NaF, KBr, LiI, etc. may be of use. The skilled artisan will realize that electrolyte solutions that do not exhibit strong Raman signals will provide minimal interference with SERS detection of nucleotides. The results demonstrate that the Raman detection system and methods disclosed above were capable of detecting and identifying single molecules of nucleotides and purine bases. This is the first report of Raman detection of unlabeled nucleotides at the single nucleotide level.

Figure 8:
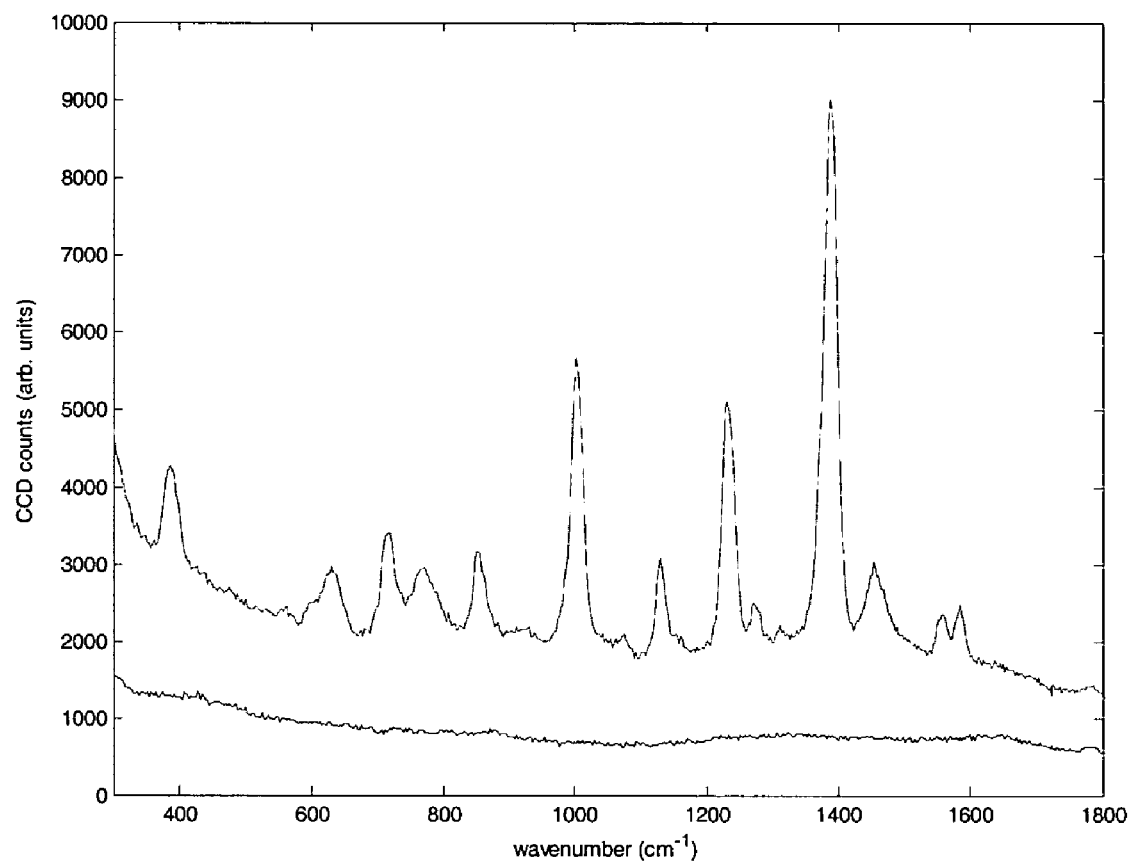
FIG. 8 shows a comparative SERS spectrum of a 500 nM solution of deoxyadenosine triphosphate covalently labeled with fluorescein (upper trace) and unlabeled dATP (lower trace). The dATP-fluorescein was obtained from Roche Applied Science (Indianapolis, Ind.). A strong increase in the SERS signal was detected in the fluorescein labeled dATP.

FIG. 8 shows the SERS spectrum of a 500 nM solution of dATP (lower trace) and fluorescein-labeled dATP (upper trace). dATP-fluorescein was purchased from Roche Applied Science (Indianapolis, Ind.). The Figure shows a strong increase in SERS signal due to labeling with fluorescein.

All of the METHODS and APPARATUS disclosed and claimed herein can be made and used without undue experimentation in light of the present disclosure. It will be apparent to those of skill in the art that variations may be applied to the METHODS and APPARATUS described herein without departing from the concept, spirit and scope of the claimed subject matter. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the claimed subject matter.

What is claimed is:

1. A method comprising:
   a) providing a porous substrate comprising a metal-coated contact surface, wherein the contact surface comprises one or more capture molecules;
   b) contacting the surface with a sample comprising one or more analytes; and
   c) using laser excitation and spectroscopy to detect and/or identify one or more analytes bound to a capture molecule.

2. The method of claim 1, wherein the substrate is a porous semiconductor substrate.

3. The method of claim 2, wherein the substrate is selected from the group consisting of nanocrystalline silicon, single crystal silicon, and polycrystalline silicon.

4. The method of claim 1, wherein metal nanoparticles are added to the metal-coated contact surface.

5. The method of claim 1, wherein the spectroscopy is Raman spectroscopy.

6. The method of claim 5, wherein the Raman spectroscopy is surface enhanced Raman spectroscopy (SERS), surface enhanced resonance Raman spectroscopy (SERRS) hyper-Raman and/or coherent anti-Stokes Raman spectroscopy (CARS).

7. The method of claim 1, wherein the analyte is selected from the group consisting of an amino acid, peptide, polypeptide, protein, glycoprotein, lipoprotein, nucleoside, nucleotide, purine, pyrimidine, oligonucleotide, nucleic acid, sugar, carbohydrate, oligosaccharide, polysaccharide, fatty acid, lipid, hormone, metabolite, cytokine, chemokine, receptor, neurotransmitter, antigen, allergen, antibody, substrate, metabolite, cofactor, inhibitor, drug, pharmaceutical, nutrient, prion, toxin, poison, explosive, pesticide, chemical warfare agent, biohazardous agent, bacteria, virus, radioisotope, vitamin, heterocyclic aromatic compound, carcinogen, mutagen, narcotic, amphetamine, barbiturate, hallucinogen, waste product and contaminant.

8. The method of claim 7, wherein the analyte is a nucleoside, nucleotide, purine, pyrimidine, oligonucleotide, nucleic acid, amino acid, peptide, polypeptide or protein.

9. The method of claim 1, wherein the one or more analytes are labeled with one or more Raman labels.

10. The method of claim 9, wherein each analyte is labeled with a distinguishable Raman label.

11. The method of claim 1, wherein the one or more capture molecules, individually or in concert, bind to one or more single nucleotides.

12. The method of claim 11, wherein the one or more capture molecules are selected from the group consisting of oligonucleotides, nucleic acids, antibodies, antibody fragments, antigens, epitopes, lectins, proteins, polypeptides, peptides, receptor proteins, ligands, hormones, vitamins, metabolites, substrates, inhibitors, cofactors, pharmaceuticals, aptamers, cytokines and neurotransmitters.

13. The method of claim 8, further comprising detecting one or more nucleotides, purines or pyrimidines at the single molecule level.

14. The method of claim 13, wherein the nucleotide, purine or pyrimidine is selected from the group consisting of adenine, adenosine monophosphate, adenosine diphosphate adenosine triphosphate, deoxyadenosine monophosphate, deoxyadenosine diphosphate and deoxyadenosine triphosphate.

15. An apparatus comprising:
   a) a nanocrystalline porous substrate comprising a metal-coated contact surface, wherein the contact surface comprises one or more capture molecules;
   b) a laser;
   c) a Raman detector adapted to detect and/or identify one or more analytes bound to the capture molecule; and
   d) a spectrometer.

16. The apparatus of claim 15, wherein the porous substrate is a support layer comprising silicon.

17. The apparatus of claim 15, wherein the porous substrate is a support layer comprising a metal.

18. The apparatus of claim 17, wherein the metal further comprises nanoparticles associated with the metal-coated surface.

19. The apparatus of claim 15, further comprising a flow through cell operably coupled to the Raman detector, wherein flow passes through the nanocrystalline porous substrate inside the flow through cell.

20. The apparatus of claim 15, wherein the substrate is produced by a method comprising thermal decomposition or microfluidic impregnation of a metal salt.

21. The apparatus of claim 15, wherein the substrate comprises a uniform metal layer.

22. The apparatus of claim 21, wherein the metal layer is at least 3 microns in depth.

23. The apparatus of claim 15, wherein the nanocrystalline substrate has at least one chamber or trench in the micron size range in the surface thereof.

24. A method comprising:
   a) providing a porous silicon substrate comprising a metal-coated contact surface, wherein the contact surface comprises one or more capture molecules;
   b) contacting the surface with a sample comprising one or more analytes; and
   c) using laser excitation and Raman spectroscopy to detect and/or identify one or more analytes bound to a capture molecule.

25. The method of claim 24, wherein the substrate is plasma-oxidized, dip and decomposed (PODD) porous silicon substrate.

26. The method of claim 24, wherein the one or more analytes are selected from the group consisting of a nucleoside, a nucleotide, a purine, a pyrimidine, an oligonucleotide, a nucleic acid, an amino acid, a peptide, a polypeptide and a protein.

27. The method of claim 26, further comprising detecting at least one purine, pyrimidine or nucleotide at the single molecule level.

28. The method of claim 27, wherein the single molecule is selected from the group consisting of adenine, adenosine monophosphate, adenosine diphosphate adenosine triphosphate, deoxyadenosine monophosphate, deoxyadenosine diphosphate and deoxyadenosine triphosphate.

29. The apparatus of claim 23, wherein the nanoparticles are nanoparticle aggregates or cross-linked nanoparticles.

* * * * *